United States Patent
Kaufman et al.

[11] Patent Number: 6,013,103
[45] Date of Patent: Jan. 11, 2000

[54] MEDIAL PIVOT KNEE PROSTHESIS

[75] Inventors: Michael E. Kaufman, Memphis; Kevin B. Hayes, Cordova; Dennis J. Buchanan, Memphis, all of Tenn.; Robert D. Paxson, Twinsburg, Ohio; Irina A. Timmerman, Bartlett, Tenn.; Stephen E. White, Cordova, Tenn.

[73] Assignee: Wright Medical Technology, Inc., Arlington, Tenn.

[21] Appl. No.: 08/979,116

[22] Filed: Nov. 26, 1997

Related U.S. Application Data

[63] Continuation-in-part of application No. 08/680,272, Jul. 11, 1996.

[51] Int. Cl.$^7$ ....................................................... A61F 2/38
[52] U.S. Cl. ................................................................. 623/20
[58] Field of Search .................................. 623/16, 18, 20

[56] References Cited

U.S. PATENT DOCUMENTS

| | | | |
|---|---|---|---|
| 4,224,696 | 9/1980 | Murray et al. .................................... | 1/3 |
| 4,353,136 | 10/1982 | Polyzoides et al. ...................... | 623/20 |
| 4,470,158 | 9/1984 | Pappas et al. ............................. | 623/20 |
| 4,714,474 | 12/1987 | Brooks, Jr. et al. .......................... | 2/38 |
| 4,759,767 | 7/1988 | Lacey ............................................. | 2/38 |
| 5,071,438 | 12/1991 | Jones et al. .................................... | 2/38 |
| 5,219,362 | 6/1993 | Tuke et al. .................................... | 2/38 |
| 5,226,916 | 7/1993 | Goodfellow et al. ...................... | 623/20 |

Primary Examiner—David J. Isabella
Attorney, Agent, or Firm—Walker, McKenzie & Walker, P.C.

[57] ABSTRACT

A knee prosthesis for replacing at least a portion of a knee joint between the distal end of a femur and the proximal end of a tibia. The knee prosthesis includes a tibial component for mounting to the proximal end of the tibia, the tibial component including a proximal surface having a semispherical medial cavity and a lateral cavity; and a femoral component for mounting to the distal end of the femur, the femoral component including a semispherical medial condylar portion for pivotally coacting with the semispherical medial cavity of the tibial component and including a semispherical lateral condylar portion for movably coacting with the lateral cavity of the tibial component; the semispherical medial condylar portion being substantially congruent with the semispherical medial cavity of the tibial component so that substantially complete surface-to-surface contact between the semispherical medial cavity of the tibial component and the semispherical medial condylar portion of the femoral component is provided throughout the range of flexion of the knee joint.

12 Claims, 15 Drawing Sheets

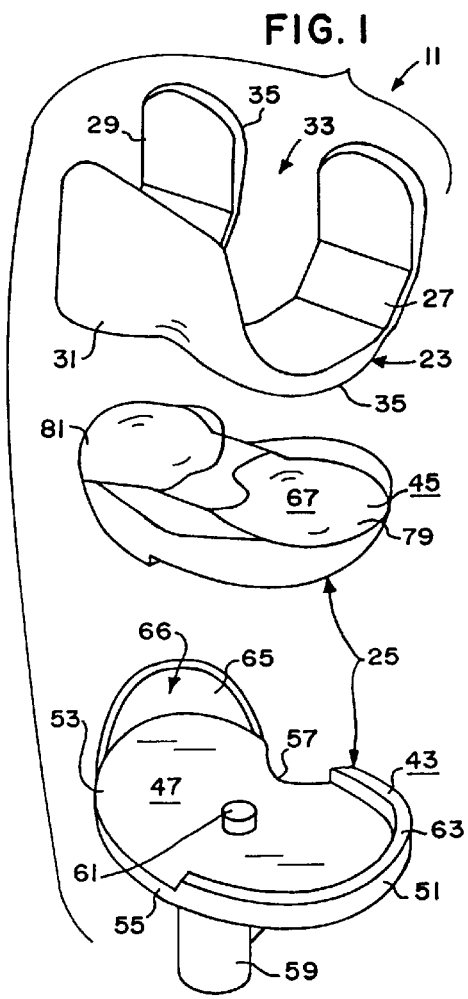
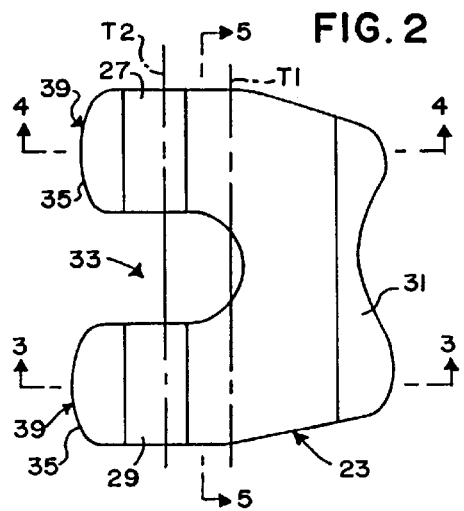
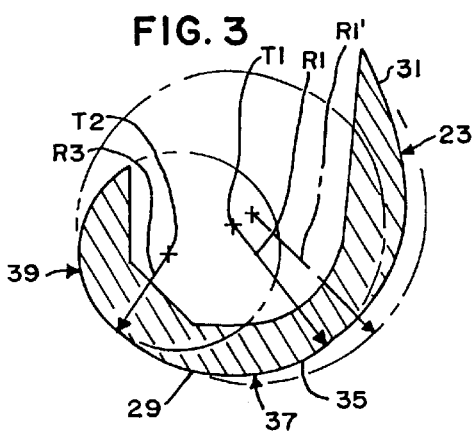
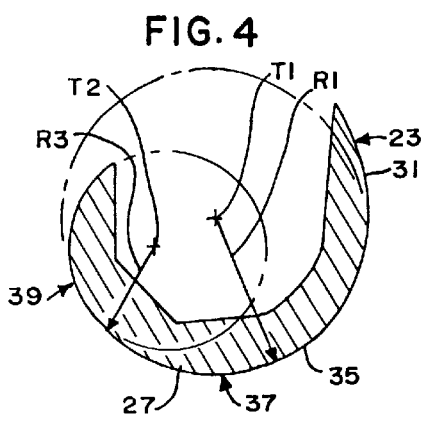
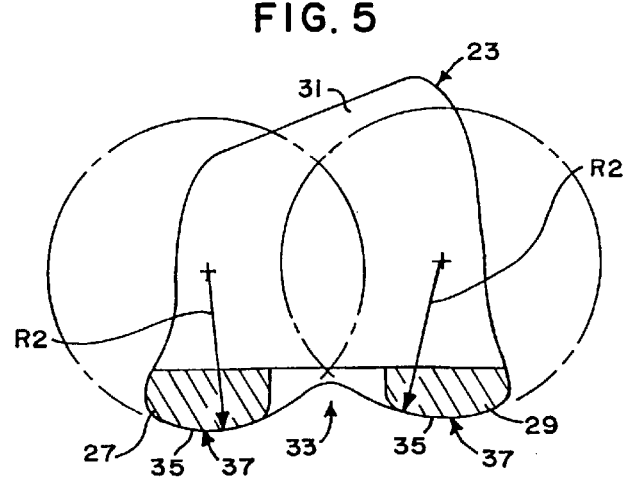

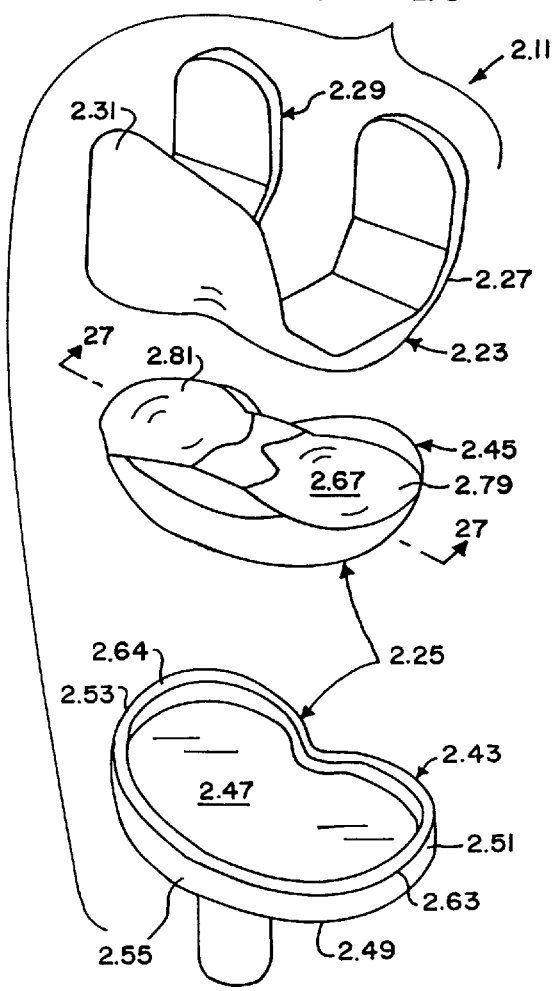
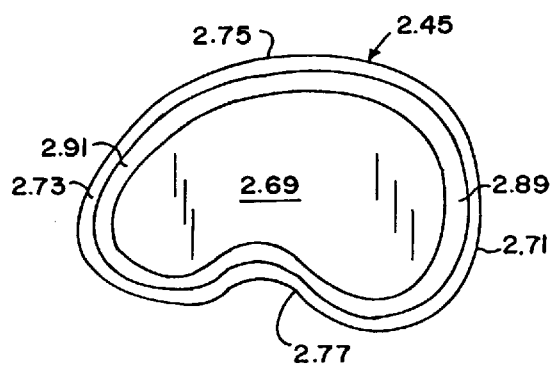
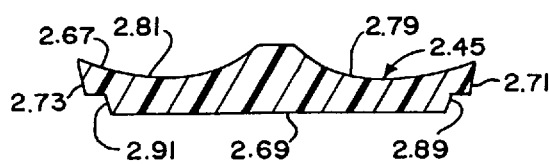
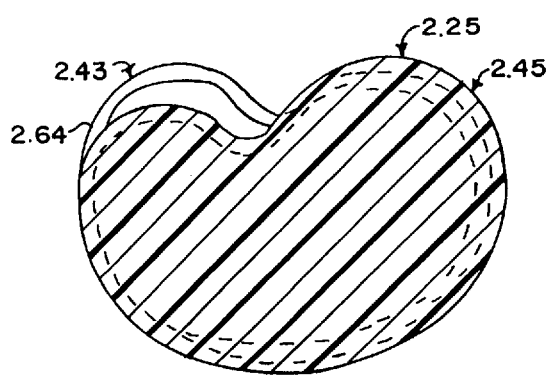
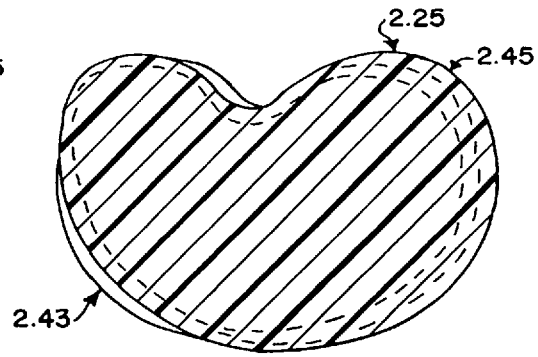

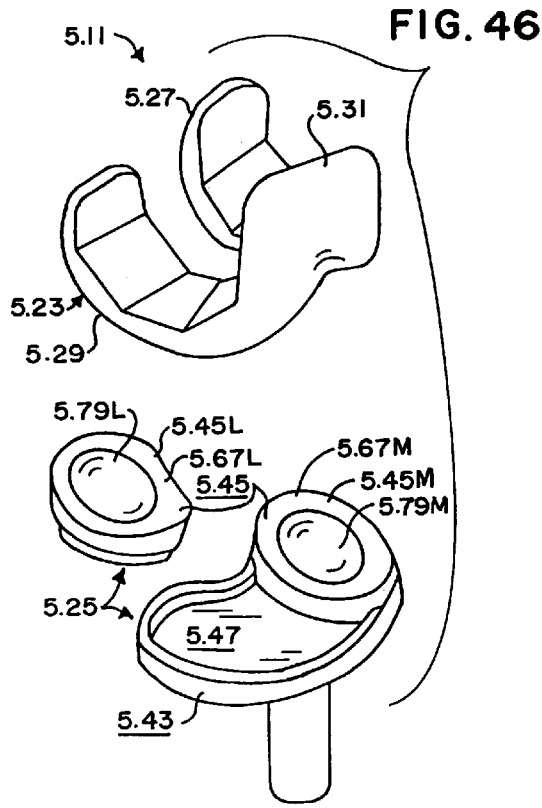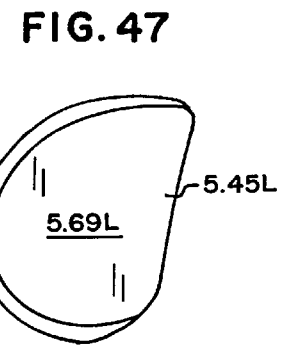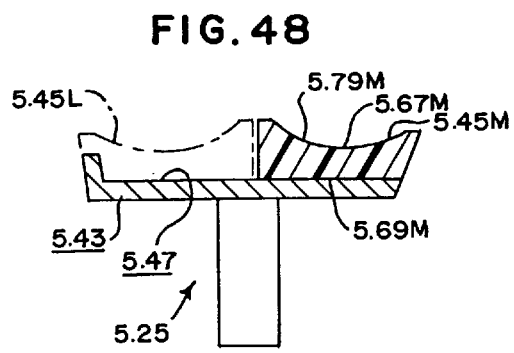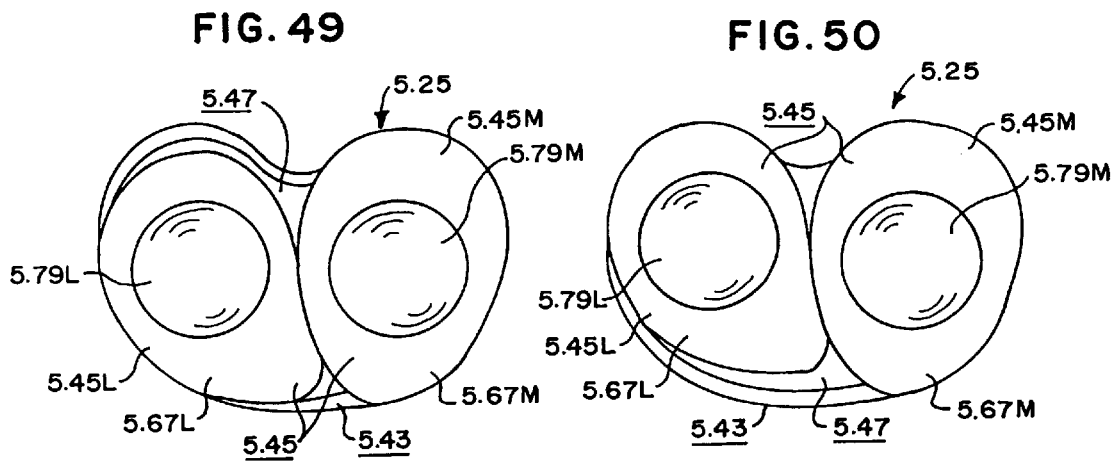

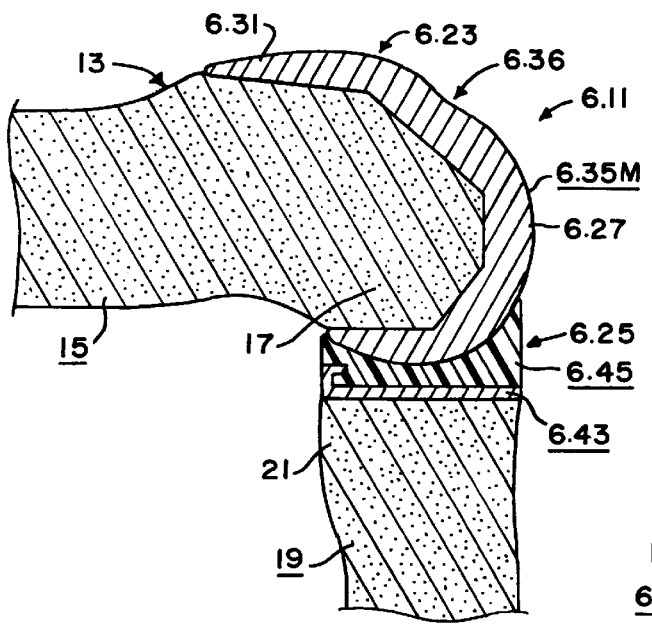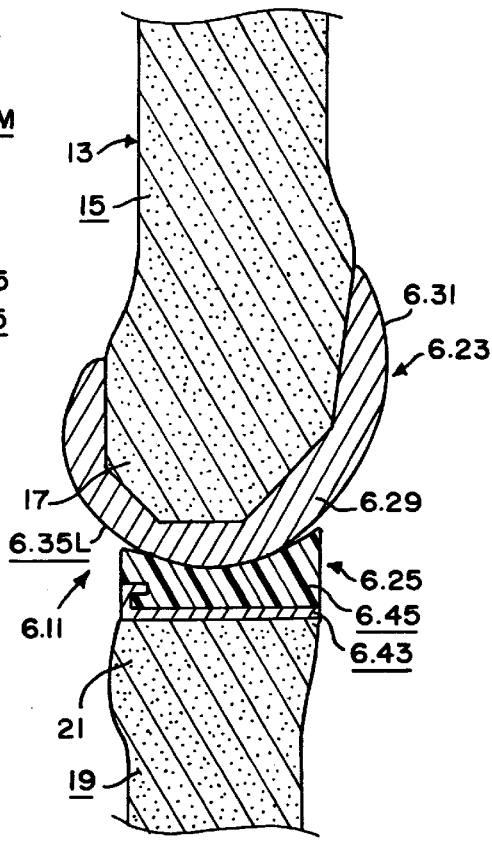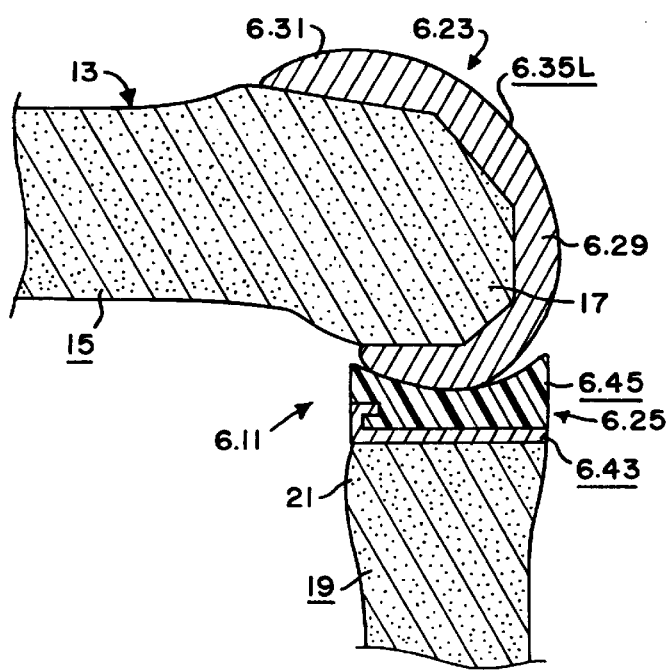

MEDIAL PIVOT KNEE PROSTHESIS

CROSS-REFERENCE TO RELATED APPLICATIONS

This application is a continuation-in-part of application Ser. No. 08/680,272, filed Jul. 11, 1996, entitled "Knee Prosthesis," now pending.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates in general to an improved knee prosthesis for replacing at least a portion of a knee joint.

2. Information Disclosure Statement

A knee prosthesis for partially or totally replacing a knee joint which has been damaged due to trauma or disease typically includes a femoral component for attachment to the distal end of a femur, and a tibial component for attachment to the proximal end of a tibia. The tibia component often includes a base or tray for being implanted in the tibia, and an insert or meniscal plate on the face of the tray for articulating with the condyles of the femoral component.

Murray et al., U.S. Pat. No. 4,224,696, issued Sep. 30, 1980, discloses a prosthetic knee including a femoral component for being attached to a femur, a tibial base for being attached to a tibia, and an insert or meniscal plate disposed between the distal plateau or face of the femoral component and the proximal plateau or face of the tibial base. The proximal plateau or face of the tibial component has a concave, compoundly curved surface while the distal face of the insert has a convex surface shaped complementary to the proximal plateau or face of the tibial component so as to permit substantially unrestrained relative sliding motion between the proximal plateau or face of the tibial component and the distal face of the insert when the two are biased against each other.

Brooks et al., U.S. Pat. No. 4,714,474, issued Dec. 22, 1987, discloses a knee joint prosthesis including a tibial component with a base for being attached to a tibia, and a removable articulating surface insert that is locked to the tibial base when implanted.

Lacey, U.S. Pat. No. 4,759,767, issued Jul. 26, 1988, discloses a tibial component of a knee prosthesis that includes a base for being attached to a tibia without bone cement, and a replaceable plateau insert for being non-movably attached to the base by the use of undercut flanges extending upward from the plateau of the base which coact with appropriate grooves in the lower face of the insert.

Jones et al., U.S. Pat. No. 5,071,438, issued Dec. 10, 1991, discloses a prosthetic knee with a tibial prosthesis comprising a baseplate and an articulating surface which pivots on the baseplate about an axis within a medial condylar compartment.

Tuke et al., U.S. Pat. No. 5,219,362, issued Jun. 15, 1993, discloses a knee prosthesis including a femoral component having a medial condyle and a lateral condyle, and a tibial component having a proximal plateau or face with a medial condyle receiving recess and a lateral condyle receiving recess. The medial condyle and medial condyle receiving recess are generally spherical. The lateral condyle receiving recess is in the form of an arcuate groove, and the curvature of the lateral condyle in the sagittal plane is formed about a pair of parallel axes such that as the knee is straightened, the lateral tibial condyle recess is cammed anteriorly, thereby allowing the tibia to rotate medially slightly about its axis as the knee is straightened from a flexed position.

Nothing in the known prior art discloses or suggests the present invention. More specifically, nothing in the known prior art discloses or suggests a knee prosthesis including a tibial component for mounting to the proximal end of the tibia, the tibial component including a proximal surface having a semispherical medial cavity and a lateral cavity; and a femoral component for mounting to the distal end of the femur, the femoral component including a semispherical medial condylar portion for pivotally coacting with the semispherical medial cavity of the tibial component and including a semispherical lateral condylar portion for movably coacting with the lateral cavity of the tibial component; the semispherical medial condylar portion being substantially congruent with the semispherical medial cavity of the tibial component so that substantially complete surface-to-surface contact between the semispherical medial cavity of the tibial component and the semispherical medial condylar portion of the femoral component is provided throughout the range of flexion of the knee joint.

BRIEF SUMMARY OF THE INVENTION

The present invention provides an improved knee prosthesis for replacing at least a portion of a knee joint between the distal end of a femur and the proximal end of a tibia.

The knee prosthesis of the present invention includes, in general, a tibial component for mounting to the proximal end of the tibia, the tibial component including a proximal surface having a semispherical medial cavity and a lateral cavity; and a femoral component for mounting to the distal end of the femur, the femoral component including a semispherical medial condylar portion for pivotally coacting with the semispherical medial cavity of the tibial component and including a semispherical lateral condylar portion for movably coacting with the lateral cavity of the tibial component; the semispherical medial condylar portion being substantially congruent with the semispherical medial cavity of the tibial component so that substantially complete surface-to-surface contact between the semispherical medial cavity of the tibial component and the semispherical medial condylar portion of the femoral component is provided throughout the range of flexion of the knee joint.

One object of the present invention is to provide a knee prosthesis specifically designed to provide substantially complete surface-to-surface contact between the face surface of a medial cavity in the upper surface of a tibial component and the face surface of a medial condylar portion of a femoral component throughout a significant portion of the range of flexion of the knee joint.

Another object of the present invention is to provide a knee prosthesis specifically designed as a medial pivot knee prosthesis by restricting the movement between of the medial condyles of the femoral and tibial components about the longitudinal axes of the femur and tibia to a pivotal movement.

Another object of the present invention is to provide a femoral implant design in which both the medial and lateral condyles have spheres or spherical portions of identical or different spherical radii.

Another object of the present invention is to provide a femoral implant design in which the medial condyle may have a single radius of curvature from 40° or more of hyperextension to 90° or more of flexion.

Another object of the present invention is to provide a femoral implant design in which the lateral condyle may have a single radius of curvature from 0° or more of hyperextension to 90° or more of flexion.

Another object of the present invention is to provide a femoral implant design in which at least the medial condyle may feature a small indentation to accommodate an anterior medial lip on the tibial insert to prevent posterior tibial subluxation.

Another object of the present invention is to provide a femoral implant design which may have a patellar groove with a constant radius of curvature to allow articulation of a highly congruent patellar implant.

Another object of the present invention is to provide a femoral implant design which may have a patellar groove that extends posteriorly to enable contact with the patellar implant to at least 100° of flexion.

Another object of the present invention is to provide a femoral implant design which may have a patellar groove that is centrally placed between the medial and lateral condyles at the beginning of the intercondylar notch and then extends laterally at an angle, for example, between 0° and 10°, preferably 3.6°.

Another object of the present invention is to provide a femoral and tibial implant design that may provide the surgeon with the flexibility to preserve or resect the posterior cruciate ligament (PCL). In the case of resection of the PCL, the knee prosthesis of the present invention offers the following advantages over a traditional PCL substitution type design (i.e., a design with a traditional cam and spine): a) the knee prosthesis of the present invention is more bone preserving as the bone in the intercondylar recess is not removed to accommodate a housing, b) the patellar groove is further extended in the knee prosthesis of the present invention since there is no housing, c) the dislocation safety factor (dsf) is approximately 11 millimeters at all angles of flexion in the knee prosthesis of the present invention whereas it is variable with flexion in a traditional PCL substitution type design.

Another object of the present invention is to provide the surgeon more latitude in terms of femorotibial alignment allowing optimal tibial bone coverage without compromise to rotational alignment.

Another object of the present invention is to provide a femoral implant that may be designed to articulate with either a traditional anterior/posterior lipped PCL sparing tibial insert, a medial pivot tibial insert, both of which assemble into and are stationary with a metal tibial base, or a mobile bearing design which may include medial pivot features. This flexibility provides the surgeon with significant versatility to treat a variety of patient indications with the same knee system and instrumentation and vary the treatment option intraoperatively easily and without compromise.

Another object of the present invention is to provide a knee prothesis than can be used in conjunction with a cam and spine to yield a more traditional PCL substitution design.

Another object of the present invention is to provide a tibial implant having a medial condyle possessing a spherical radius that matches the spherical radius of the medial condyle of the femoral implant to create a ball and socket joint.

Another object of the present invention is to provide a tibial implant that may have anterior and posterior lips dimensioned to provide adequate intrinsic stability comparable to a more traditional PCL substitution design, especially at flexion angles less than 90°.

Another object of the present invention is to provide a tibial implant that may have a lateral condyle that possesses the same spherical radius as the lateral condyle of the femoral implant in the frontal plane only to provide a spherical radius that sweeps an arcuate path in the transverse plane, allowing the tibial to rotate, for example, 5° internally and 10° externally with respect to the femur.

Another object of the present invention is to provide a tibial implant that may have a gentle anterior radiused groove to accommodate the patellar ligament to prevent impingement.

Another object of the present invention is to provide a tibial implant that may have a PCL cutout to allow the PCL to be preserved, if desired.

Another object of the present invention is to provide a tibial implant that may have a spherical radius in the medial condyle located in the posterior one third of the tibial insert to enable large degrees of flexion without anterior/posterior translation on the medial side, to more closely simulate the normal knee and reduce shear stresses on the tibial insert.

Another object of the present invention is to provide a very large contact area between the medial condyles of the femoral and tibial implants to reduce stress on the tibial insert (60% to 70% of the knee joint load passes through the medial condyle).

Another object of the present invention is to provide a knee prothesis with means to control anterior-posterior translation of the femur and the tibia especially on the medial condyle.

BRIEF DESCRIPTION OF THE SEVERAL VIEWS OF THE DRAWINGS

FIG. 1 is an exploded perspective view of a right knee prosthesis, illustrating a first preferred embodiment of the present invention, the left knee prosthesis being a substantial mirror image thereof.

FIG. 2 is a top plan view of a femoral component of the knee prosthesis of FIG. 1.

FIG. 3 is a sectional view substantially as taken on line 3—3 of FIG. 2, with portions omitted for clarity.

FIG. 4 is a sectional view substantially as taken on line 4—4 of FIG. 2.

FIG. 5 is a sectional view substantially as taken on line 5—5 of FIG. 2.

FIG. 25 is an exploded perspective view of a right knee prosthesis, illustrating a second preferred embodiment of the present invention, the left knee prosthesis being a substantial mirror image thereof.

FIG. 26 is a bottom plan view of an articular bearing of the tibial component of the knee prosthesis of FIG. 25.

FIG. 27 is a sectional view substantially as taken on line 27—27 of FIG. 25, with portions thereof omitted for clarity.

FIG. 28 is a somewhat diagrammatic sectional view similar to FIG. 23 but showing the articular bearing member of the tibial component of the knee prosthesis of FIG. 25 substantially fully rotated in an anterior direction with respect to the base member of the tibial component, and with portions omitted for clarity.

FIG. 29 is a somewhat diagrammatic sectional view similar to FIG. 24 but showing the articular bearing member of the tibial component of the knee prosthesis of FIG. 25 substantially fully rotated in a posterior direction with respect to the base member of the tibial component, and with portions omitted for clarity.

FIG. 46 is an exploded perspective view of a right knee prosthesis, illustrating a fifth preferred embodiment of the present invention, the left knee prosthesis being a substantial mirror image thereof.

FIG. 47 is a bottom plan view of a lateral articular bearing of the tibial component of the knee prosthesis of FIG. 46.

FIG. 48 is a sectional view substantially as taken on line 48—48 of FIG. 46, with portions thereof omitted for clarity and with the lateral articular bearing shown in broken lines.

FIG. 49 is a somewhat diagrammatic sectional view similar to FIGS. 23 and 28 but showing the lateral articular bearing member of the tibial component of the knee prosthesis of FIG. 46 substantially fully rotated in an anterior direction with respect to the base member of the tibial component, and with portions omitted for clarity.

FIG. 50 is a somewhat diagrammatic sectional view similar to FIGS. 24 and 29 but showing the lateral articular bearing member of the tibial component of the knee prosthesis of FIG. 46 substantially fully rotated in a posterior direction with respect to the base member of the tibial component, and with portions omitted for clarity.

FIG. 72 is similar to FIG. 71 but shows the knee joint flexed substantially 90 degrees.

FIG. 73 is a somewhat diagrammatic sagittal sectional view of the femoral and tibial components of knee prosthesis of FIG. 51, taken substantially along the lateral condyle of the femoral component and shown implanted in a knee joint with the knee joint substantially fully extended.

FIG. 74 is similar to FIG. 73 but shows the knee joint flexed substantially 90 degrees.

DETAILED DESCRIPTION OF THE INVENTION

Figure 6:
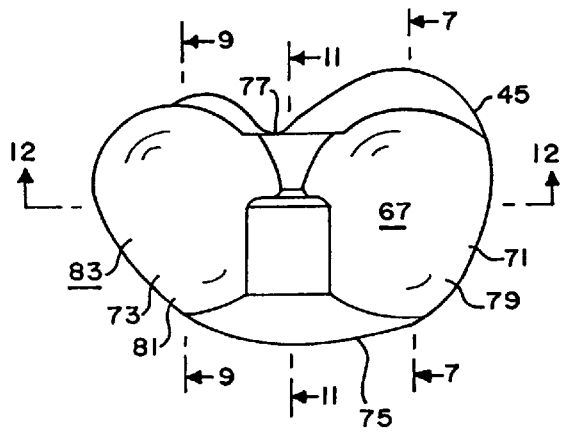
FIG. 6 is a top plan view of an articular bearing member of the tibial component of the knee prosthesis of FIG. 1.
Figure 7:
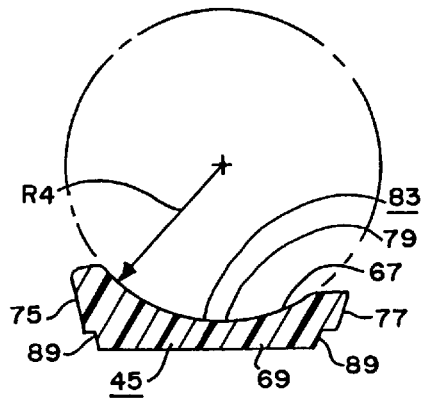
FIG. 7 is a sectional view substantially as taken on line 7—7 of FIG. 6, with portions thereof omitted for clarity.
Figure 8:
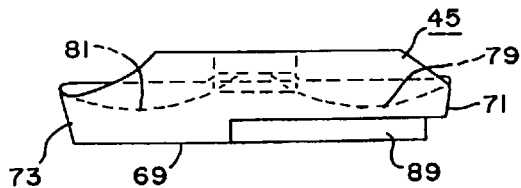
FIG. 8 is a front or anterior elevational view of an articular bearing member of FIG. 6.
Figure 9:
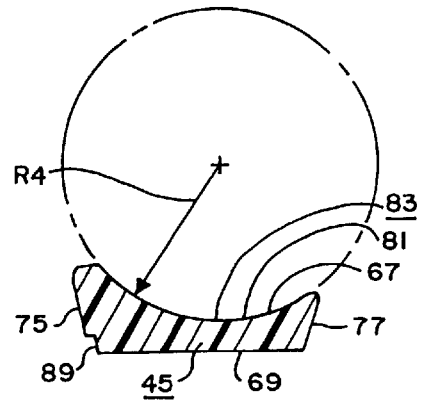
FIG. 9 is a sectional view substantially as taken on line 9—9 of FIG. 6, with portions thereof omitted for clarity.
Figure 10:
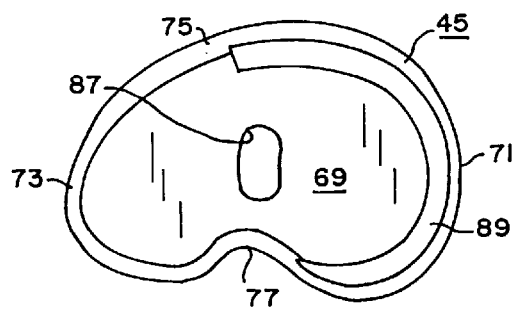
FIG. 10 is a bottom plan view of the articular bearing member of FIG. 6.
Figure 11:
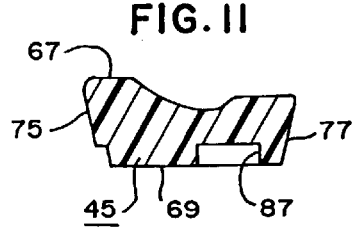
FIG. 11 is a sectional view substantially as taken on line 11—11 of FIG. 6, with portions thereof omitted for clarity.

A first preferred embodiment of the knee prosthesis of the present invention is shown generally in FIGS. 1–24 and identified by the numeral 11. The knee prosthesis 11 is designed to replace at least a portion of a knee joint 13 between the distal end 17 of a femur 15 and the proximal end 21 of a tibial 19.

The knee prosthesis 11 includes a femoral component 23 for mounting to the distal end 17 of the femur 15, and a tibial component 25 for mounting to the proximal end 21 of the tibia 19 and for articulating with the femoral component 23.

Figure 18:
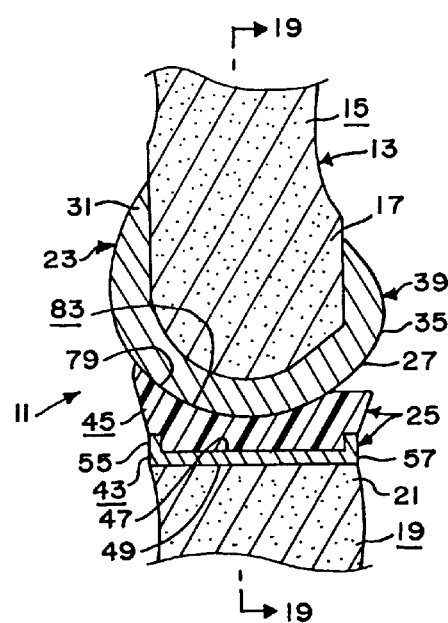
FIG. 18 is a somewhat diagrammatic sagittal sectional view of the knee prosthesis of FIG. 1, shown implanted in a knee joint with the knee joint substantially fully extended.
Figure 19:
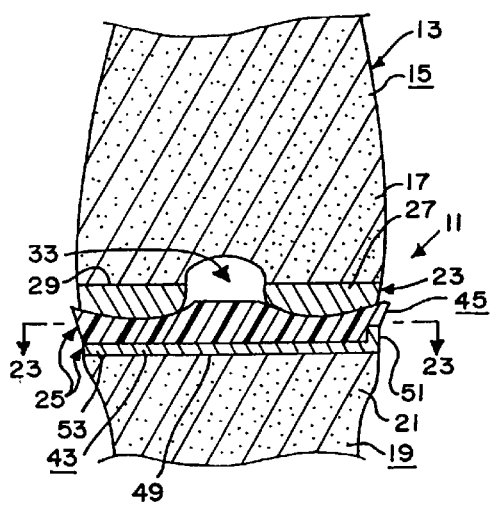
FIG. 19 is a somewhat diagrammatic sectional view substantially as taken on line 19—19 of FIG. 17 with portions thereof omitted for clarity.
Figure 20:
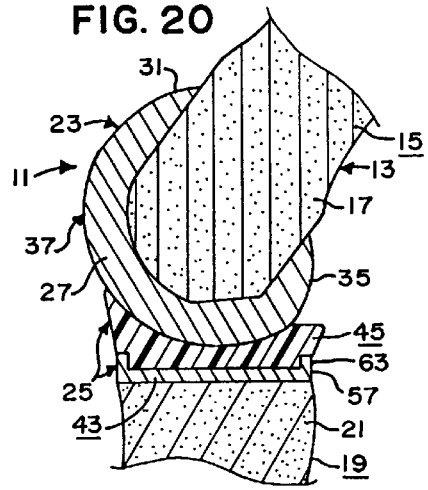
FIG. 20 is similar to FIG. 18 but shows the knee joint partially flexed.
Figure 21:
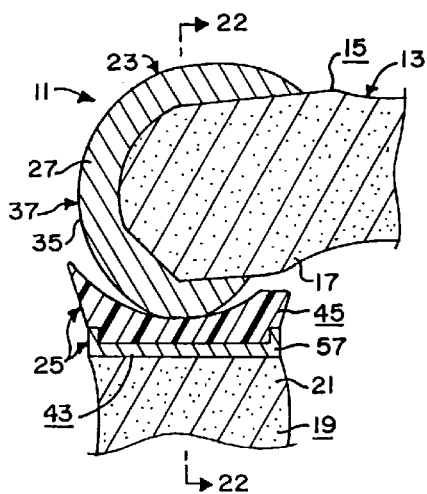
FIG. 21 is similar to FIG. 18 but shows the knee joint flexed substantially 90 degrees.
Figure 22:
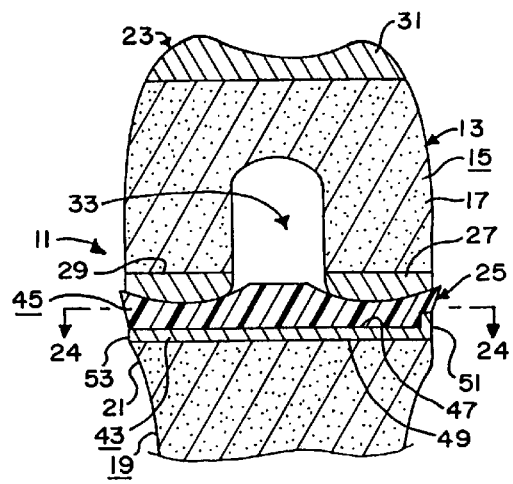
FIG. 22 is a somewhat diagrammatic sectional view substantially as taken on line 22—22 of FIG. 21 with portions thereof omitted for clarity.

The femoral component 23 preferably includes a medial condylar portion 27, a lateral condylar portion 29, and a patellar flange portion 31 joining the anterior ends of the medial and lateral condylar portions 27, 29 together with the medial and lateral condylar portions 27, 29 substantially parallel to and spaced apart from one another to form an intercondylar notch or recess 33 therebetween as clearly shown in the drawings. Each condylar portion 27, 29 has an outer or face surface 35 for articulatingly engaging a portion of the tibial component 25 as will hereinafter become apparent. The face surface 35 of each condylar portion 27, 29 preferably has a distal portion 37 for articulatingly engaging a portion of the tibial component 25 when the knee joint 13 is extended and partially flexed as shown in FIGS. 18 and 20, and a posterior portion 39 for articulatingly engaging a portion of the tibial component 25 when the knee joint 13 is flexed substantially 90° as shown in FIG. 21. The distal portion 37 of the face surface 35 is defined by a precise distal sagittal curvature formed by the radius R1 shown in FIGS. 3 and 4, and a precise distal coronal curvature formed by the radius R2 shown in FIG. 5. The posterior portion 39 of the face surface 35 is defined by a precise posterior sagittal curvature formed by the radius R3 shown in FIGS. 3 and 4 and a posterior coronal curvature shown in FIG. 22. The radius R1 is preferably the same size as the radius R2 so that the distal portion 37 of the face surface 35 forms a semispherical shape. The radius R3 is preferably smaller than the radii R1, R2. Thus, for example, the radii R1, R2 may be 1.25 inches (3.175 centimeters) while the radius R3 may be 0.75 inches (1.905 centimeters). The curvatures of the distal portions 37 of the face surface 35 of the medial and lateral condylar portions 27, 29 of the femoral component 23 in a substantially sagittal plane are formed about a center point on a distal or first transverse axis T1 that passes through the center of curvature of both distal portions 37. Similarly, the curvatures of the posterior portions 39 of the face surface 35 of the medial and lateral condylar portions 27, 29 of the femoral component 23 in a substantially sagittal plane are formed about a center point on a posterior or second transverse axis T2 that passes through the center of curvature of both posterior portions 39. As clearly shown in FIG. 2, the first and second transverse axes T1, T2 preferably extend parallel to one another with the second transverse axis T2 preferably located posteriorly of the first transverse axis T1. As illustrated in FIGS. 3 and 4, the second transverse axis T2 is also preferably located distally of the first transverse axis T1. Each condylar portion 27, 29 may be substantially identical, or symmetric, to one another. That is, the distal sagittal and coronal curvatures R1, R2 of the lateral condylar portion 29 of the femoral component 23 preferably matches the distal sagittal and coronal curvatures R1, R2 of the medial condylar portion 27 of the femoral component 23, with the transverse axis T1 extending along a transverse plane, etc. On the other hand, the condylar portions 27, 29 may be asymmetric to one another. That is, face surface 35 of the lateral condylar portion 29 of the femoral component 23 may be designed so that it does not match of the face surface of the medial condylar portion 27 of the femoral component 23. For example, the distal sagittal and/or coronal curvatures R1, R2 of the lateral condylar portion 29 of the femoral component 23 may be larger than the respective distal sagittal and/or coronal curvatures R1, R2 of the lateral condylar portion 29 of the femoral component 23, or may be formed about a center point that is not on the same transverse plane as the center point about which the respective distal sagittal and/or coronal curvatures R1, R2 of the lateral condylar portion 29 of the femoral component 23 are formed, etc. Thus, the distal sagittal curvature R1' of an alternative lateral condylar portion 29 as shown in broken lines in FIG. 3 may be based on a larger radius than the distal sagittal curvature R1 of the medial condylar portion 27 as shown in FIG. 4.

The patellar flange portion 31 may be asymmetric as clearly shown in FIGS. 1, 2, and 5, or may be symmetric as will now be apparent to those skilled in the art.

The femoral component 23 may include typical attachment aids for helping to secure the femoral component 23 to the distal end 17 of the femur 15. Such attachment aids may include one or more pegs, fins, surface treatments, etc., as will now be apparent to those skilled in the art.

The femoral component 23 may be constructed in various manners and out of various materials as will now be apparent to those skilled in the art. Thus, for example, the femoral component 23 can be machined, cast, forged or otherwise constructed as a one-piece, integral unit out of a medical grade, physiologically acceptable metal such as a cobalt chromium alloy or the like, in various sizes to fit a range of typical patients, or may be custom-designed for a specific patient based on data provided by a surgeon after physical and radiography examination of the specific patient, etc.

The tibial component 25 includes a base or tray member 43 for being secured to the proximal end 21 of the tibia 19, and an articular bearing, insert or superstructure member 45 for being movably mounted on the base member 43.

The base member 43 has an upper or proximal surface 47, a lower or distal surface 49, a medial side 51, a lateral side 53, an anterior or front side 55, and a posterior or rear side 57. The upper surface 47 may be substantially flat and planar as shown in the drawings. The base member 43 preferably includes attachment aids 59 for helping to secure the base member 43 to the proximal end 21 of the tibia 19. Such attachment aids 59 may include one or more pegs, fins, screws, surface treatments, etc., on the lower surface 49 thereof as will now be apparent to those skilled in the art. As clearly shown in FIGS. 14 and 16, a peg-like attachment aid 59 thereof may have an aperture therein for allowing extensions to be attached thereto for extending into the intramedullary canal of the tibia 19, etc., as will now be apparent to those skilled in the art.

Figure 12:
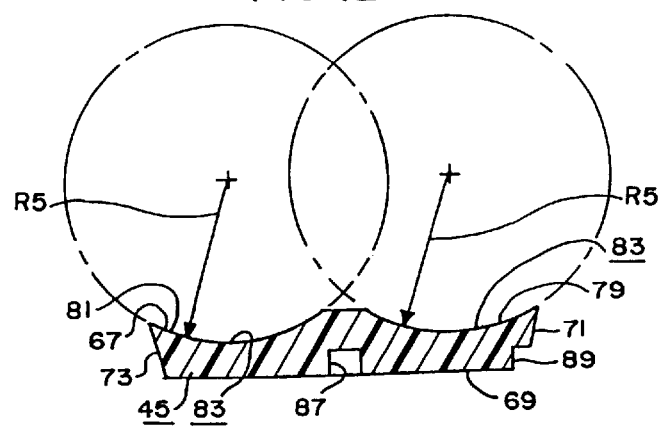
FIG. 12 is a sectional view substantially as taken on line 12—12 of FIG. 6, with portions thereof omitted for clarity.
Figure 13:
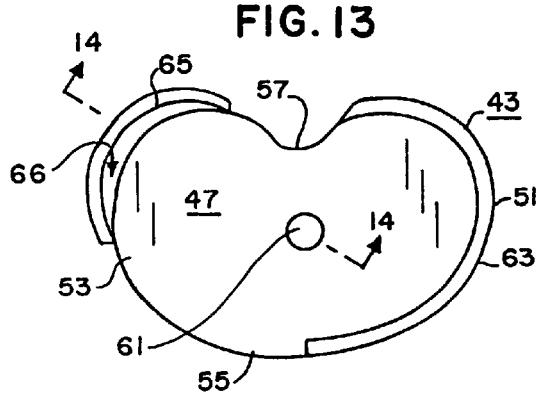
FIG. 13 is a top plan view of a base member of the tibial component of the knee prosthesis of FIG. 1.
Figure 14:
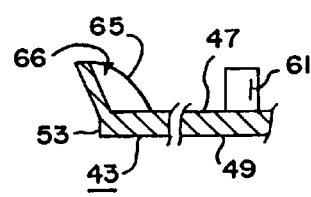
FIG. 14 is a sectional view substantially as taken on line 14—14 of FIG. 13, with portions thereof omitted for clarity.
Figure 15:
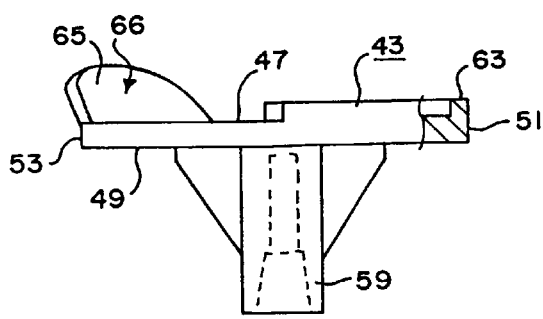
FIG. 15 is a front or anterior elevational view of the base member of FIG. 13, with portions thereof broken away for clarity.
Figure 16:
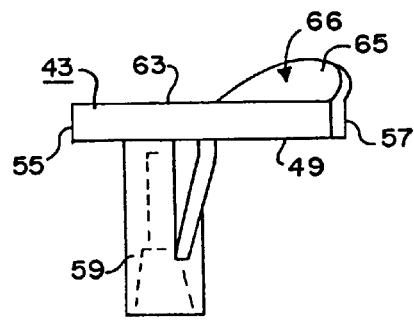
FIG. 16 is a medial side elevational view of the base member of FIG. 13.
Figure 17:
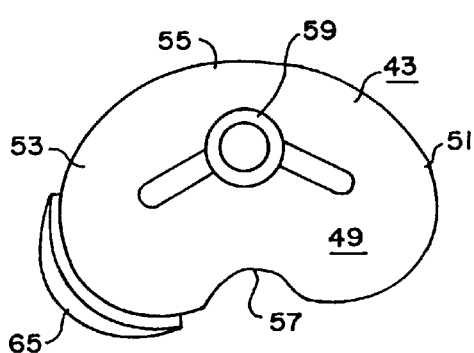
FIG. 17 is a bottom plan view of the base member of FIG. 13.

The base member 43 may include a boss or pin 61 extending upward from the upper surface 47 thereof substantially centrally of the upper surface 47 as clearly shown in FIGS. 1 and 12, a medial ledge or wall 63 extending upward from the upper surface 47 thereof adjacent the medial side 51 thereof and extending generally from substantially the midportion of the anterior side 55 around the medial side 51 and to substantially the midportion of the posterior side 57 thereof (i.e., along the posterior/medial quadrant, the medial side, and the anterior/medial quadrant of the upper surface 47 of the base member 43), and a lateral fin 65 extending upward and outward from the upper surface 47 thereof adjacent the lateral side 53 thereof and extending generally from substantially the midportion of the lateral side 53 and to substantially the midportion of the posterior side 57 thereof (i.e., along the posterior/lateral quadrant of the upper surface 47 of the base member 43). The lateral fin 65 preferably has a rounded upper edge to form a lip and coacts with the lateral side 53 of the base member 43 to form a groove-like outer surface 66 (see FIG. 13) to provide a bearing or articulating surface against which the popliteus muscle of the leg can ride after the knee prosthesis 11 is implanted as will now be apparent to those skilled in the art.

The base member 43 may be constructed in various manners and out of various materials as will now be apparent to those skilled in the art. Thus, for example, the base member 43 can be machined or otherwise constructed as a one-piece, integral unit out of a medical grade, physiologically acceptable metal such as a cobalt chromium alloy or the like, in various sizes to fit a range of typical patients, or may be custom-designed for a specific patient based on data provided by a surgeon after physical and radiography examination of the specific patient, etc. The upper surface 47 may be polished for reasons which will hereinafter become apparent.

The articular bearing member 45 has an upper or proximal surface 67, a lower or distal surface 69, a medial side 71, a lateral side 73, an anterior or front side 75, and a posterior or rear side 77. The lower surface 69 may be substantially flat and planar as shown in the drawings for matingly and confrontingly contacting the upper surface 47 of the base member 43. The sides 71, 73, 75, 77 of the articular bearing member 45 preferably generally angle upward and outward from the lower surface 69 to the upper surface 67 thereof.

The upper surface 67 of the articular bearing member 45 preferably has a medial concavity 79 for pivotally receiving and coacting with the face surface 35 of the medial condylar portion 27 of the femoral component 23, and a lateral concavity 81 for pivotally receiving and coacting with the face surface 35 of the lateral condylar portion 29 of the femoral component 23. The medial and lateral concavities 79, 81 are similar to one another and each has a face surface 83 for articulatingly receiving a portion of the face surface 35 of the respective condylar portion 27, 29 of the femoral component 23 as will hereinafter become apparent. The face surface 83 of each concavity 79, 81 is preferably defined by a precise proximal sagittal curvature formed by the radius R4 shown in FIGS. 7 and 9, and a precise proximal coronal curvature formed by the radius R5 shown in FIG. 12. The radius R4 is preferably the same size as the radius R5 so that the face surface 83 forms a semispherical shape. In addition, the radii R4, R5 are preferably substantially congruent with or approximately the same size as the radii R1, R2, with appropriate clearances, so that there is substantially complete surface-to-surface contact between the face surfaces 35, 83 throughout a significant portion of the range of flexion of the knee joint 13, for example, between full extension of the knee joint 13 as shown in FIG. 18 and approximately 60° of flexion of the knee joint 13 as illustrated in FIG. 20.

Figure 23:
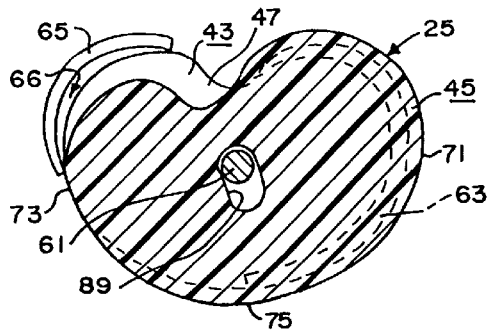
FIG. 23 is a somewhat diagrammatic sectional view substantially as taken on line 23—23 of FIG. 19, showing the articular bearing member of the tibial component substantially fully rotated in an anterior direction with respect to the base member of the tibial component, and with portions omitted for clarity.
Figure 24:
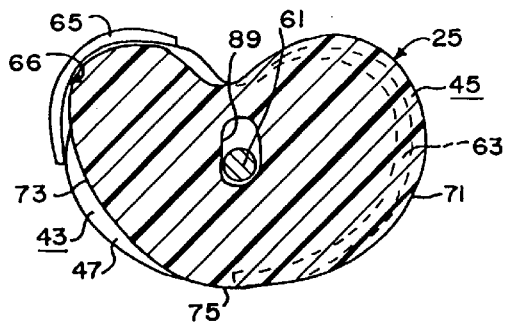
FIG. 24 is a somewhat diagrammatic sectional view substantially as taken on line 24—24 of FIG. 22, showing the articular bearing member of the tibial component substantially fully rotated in a posterior direction with respect to the base member of the tibial component, and with portions omitted for clarity.
Figure 30:
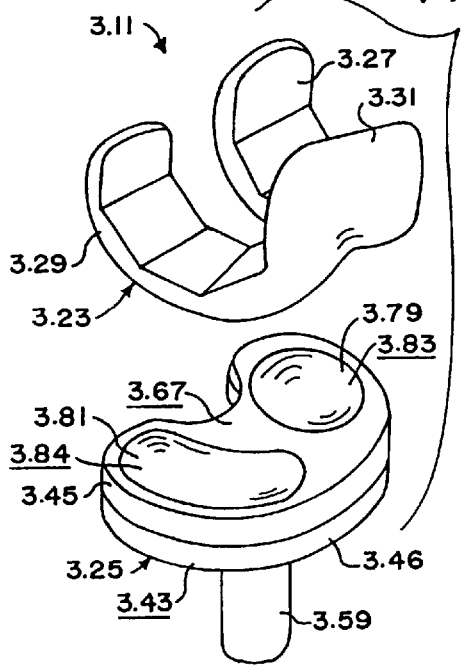
FIG. 30 is an exploded perspective view of a right knee prosthesis, illustrating a third preferred embodiment of the present invention, the left knee prosthesis being a substantial mirror image thereof.

The articular bearing member 45 preferably has a slot 87 in the lower surface 69 thereof for receiving the pin 61 of the base member 43. The slot 87 is preferably dimensioned to loosely receive the pin 61 to thereby allow the articular bearing member 45 to pivot and slide on the base member 43 and may be curved somewhat about a center on the lateral side of the articular bearing member 45 as shown in FIGS. 23 and 24.

The articular bearing member 45 preferably has a medial groove 89 for guidingly receiving the medial ledge 63 of the base member 43. The medial groove 89 preferably extends upward from the lower surface 69 thereof adjacent the medial side 71 thereof and extending generally from substantially the midportion of the anterior side 75 around the medial side 71 and to substantially the midportion of the posterior side 77 thereof (i.e., along the posterior/medial quadrant, the medial side, and the anterior/medial quadrant of the lower surface 69 of the articular bearing member 45).

The articular bearing member 45 may be constructed in various manners and out of various materials as will now be apparent to those skilled in the art. Thus, for example, the articular bearing member 45 can be machined, molded or otherwise constructed as a one-piece, integral unit out of a medical grade, physiologically acceptable plastic such as an ultra high molecular weight polyethylene or the like, in various sizes to fit a range of typical patients, or may be custom-designed for a specific patient based on data provided by a surgeon after physical and radiography examination of the specific patient, etc. With the articular bearing member 45 constructed out of ultra high molecular weight polyethylene or the like, it will freely slide on the polished upper surface 47 of the base member 43.

The tibial component 25 includes restriction means for restricting the slidable movement of the articular bearing member 45 relative to the base member 43 to allow a swinging motion of the lateral portion of the upper surface 67 of the articular bearing member 45 and a pivotal motion of the medial portion of the upper surface 67 of the articular bearing member 45. The restriction means may be designed to restrict the pivoting motion of the articular bearing member 45 to approximately 20 degrees of internal/external rotation of the knee joint 13 as will now be apparent to those skilled in the art. The restriction means may be constructed or formed by various structure.

For example, the articular bearing member 45 may have a spherical dome or boss (not shown) extending inferiorly from the lower surface 69 substantially beneath the medial concavity 79 in the upper surface 67 thereof, and the base member 43 may have a matching depression (not shown) in the upper surface 47 thereof on its medial side, thereby permitting the articular bearing member 45 to pivot about the axis of the medial dome and depression. However, it should be understood that such specific construction of the restriction means can be reversed by forming the dome on the upper surface 47 of the base member 43 and by forming the mating recess in the lower surface 69 of the articular bearing member.

Alternately, the restriction means can be formed or defined by two small diameter pins (not shown) extending upwardly from the upper surface 47 of the base member 43, each post being centered generally beneath one of the medial or lateral concavities 79, 81 of the upper surface 67 of the articular bearing member 45, a cylindrical recess (not shown) on the medial side of the lower surface 69 of the articular bearing member 45 for pivotally receiving one of the posts, and a curved slot (not shown) on the lateral side of the lower surface 69 extending generally in the anterior/posterior direction and formed on a radius from the center of the cylindrical recess for pivotally receiving the other post. The cylindrical recess and curved slot both preferably have a width greater than the diameter of the respective posts for slidably receiving the posts. This construction allows the medial portion of the articular bearing member 45 to slide in a substantially coronal or horizonal plane with respect to the base member 43 by an amount permitted by the respective width differences of the post and cylindrical recess and/or slot, and allow the lateral portion of the articular bearing member 45 to slide with respect to the base member 43 in the medial/lateral direction by the respective width differences of the post and cylindrical recess and/or slot, and in the anterior/posterior direction by the length of the slot. However, it should be understood that such specific construction of the restriction means can be reversed by providing the pins on the lower surface 69 of the articular bearing member and by forming the mating cylindrical recess and slot in the upper surface 47 of the base member 43.

Preferably, however, the restriction means is formed or defined by the coaction of the pin 61, medial ledge 63, and lateral fin 65 of the base member 43, and the slot 87 and medial groove 89 of the articular bearing member 45. This design allows a general swinging motion of the lateral portion of the articular bearing member 45 anteriorly and posteriorly while the medial portion of the articular bearing member 45, although permitted some translational movement with respect to the base member 43, is more stationary. However, it should be understood that such specific construction of the restriction means can be reversed by forming the slot 87 in the upper surface 47 of the base member 43, by providing the pin 61 on the lower surface 69 of the articular bearing member 45, by providing the medial ledge 63 and lateral fin 65 on the lower surface 69 of the articular bearing member 45, and by forming the medial groove 89 in the upper surface 47 of the base member 45, etc.

The method of replacing a knee joint 13 using the joint prosthesis 11 of the present invention typically starts with standard preoperative planning to estimate the size of the prosthesis to be implanted. The knee joint 13 can then be exposed in any typical manner. The distal end 17 of the femur 15 and the proximal end 21 of the tibia 19 can then be resected and prepared, and a trial reduction of the knee joint 13 performed using appropriate trial implants. Upon successful trial reduction, an appropriate femoral component 23 is implanted on the prepared distal end 17 of the femur 15, and an appropriate base member 43 is implanted on the prepared proximal end 21 of the tibia 19. An appropriate articular bearing member 45 is mounted on the base member 43. After final testing for motion and stability, the surgical site can be closed in any typical manner.

The joint prosthesis 11 thus providesa tibial base member 43 bearing a tibial articular bearing member 45 that is permitted a degree of movement on the base member 43. By shaping the curvatures of the medial and lateral condylar portions 27, 29 to precisely match the curvatures of the medial and lateral concavities 79, 81, respectively, of the upper surface 67 of the articular bearing member 45, the medial and lateral condylar portions 27, 29 and the medial and lateral concavities 79, 81, respectively, will stay in perfect surface-to-surface contact when the knee joint 13 is flexed such that only a single axis of movement in extension/flexion is provided as the knee joint 13 is flexed and extended. By sizing the pin 61 of the base member 43 somewhat smaller than the slot 87 in the lower surface 69 of the articular bearing member 45 [for example, by sizing the pin 61 with a 0.250 inch (6.35 millimeters) diameter and by sizing the slot 87 with a 0.300 inch (7.62 millimeters) width], and by slightly curving the slot 87 in the anterior/posterior direction (for example, about a radius of 0.689 inches (approximately 17.5 millimeters), the lateral portion of the articular bearing member 45 is permitted a general swinging motion anteriorly and posteriorly while the medial portion of the articular bearing member 45, although permitted some translational movement with respect to the base member 43, is more stationary. The coaction between the medial ledge 63 of the base member 43 and the medial groove 89 of the articular bearing member 45, and between the lateral fin 65 of the base member 43 and the lateral and posterior sides 73, 77 of the articular bearing member 45 will further restrict and define the free movement of the articular bearing member 45 relative to the base member 43.

As thus constructed and used, the knee prosthesis 11 provides a prosthesis in which the movement of the tibial articular bearing member 45 with respect to the tibial base member 43 is restrained by three constraints. The first is a pin and slot arrangement between the articular bearing member 45 and the tibial base member 43. The second is an upstanding ledge formed along the medial edge of the tibial base member 43 and against which the tibial articular bearing member 45 may abut in its movement. The third restraint is an upstanding and outwardly slanting ledge provided along the posterior lateral quadrant of the tibial base member 43; the inner surface of this ledge extends superiorly and laterally from its attachment to the tibial base member 43, and the tibial articular bearing member 45 is similarly configured so as to come into substantial surface-to-surface contact with the inner surface of the ledge. The knee prosthesis 11 provides such a prosthesis having an upstanding and outwardly slanting ledge provided along the posterior lateral quadrant of the tibial base with an upper edge that is rounded to form a lip, and with an outside surface that is grooved slightly below the lip to thus configure the lip to be a bearing surface or articulating surface against which rides the popliteus.

A second preferred embodiment of the knee prosthesis of the present invention is shown generally in FIGS. 25–29 and identified by the numeral 2.11. The knee prosthesis 2.11 is also designed to replace at least a portion of a knee joint 13 between the distal end 17 of a femur 15 and the proximal end 21 of a tibial 19.

The knee prosthesis 2.11 includes a femoral component 2.23 for mounting to the distal end 17 of the femur 15, and a tibial component 2.25 for mounting to the proximal end 21 of the tibia 19 and for articulating with the femoral component 2.23.

The femoral component 2.23 may be identical to the femoral component 23 and includes, in general, a medial condylar portion 2.27, a lateral condylar portion 2.29, and a patellar flange portion 2.31. Reference should be made to the above disclosure of the femoral component 23 for a complete and thorough understanding of the construction and function of the femoral component 2.23.

The tibial component 2.25 is preferably similar to the tibial component 25 and includes a base or tray member 2.43 for being secured to the proximal end 21 of the tibia 19, and an articular bearing, insert or superstructure member 2.45 for being movably mounted on the base member 2.43.

The base member 2.43 has a substantially flat and planar upper surface 2.47, a lower or distal surface 2.49, a medial side 2.51, a lateral side 2.53, an anterior or front side 2.55, and a posterior or rear side 2.57, and is otherwise similar to the base member 43. However, as clearly shown in FIG. 25, the base member 2.43 does not include a boss or pin extending upward from the upper surface 2.47 thereof such as the pin 61 of the base member 43. The base member 2.43 has a medial ledge or wall 2.63 extending upward from the upper surface 2.47 thereof adjacent the medial side 2.51 thereof and extending generally from substantially the midportion of the anterior side 2.55 around the medial side 2.51 and to substantially the midportion of the posterior side 2.57 thereof (i.e., along the posterior/medial quadrant, the medial side, and the anterior/medial quadrant of the upper surface 2.47 of the base member 2.43), similar to the medial ledge 63 of the base member 43. However, the base member 2.43 additionally has a lateral ledge or wall 2.64 extending upward from the upper surface 2.47 thereof adjacent the lateral side 2.53 thereof and extending generally from substantially the midportion of the anterior side 2.55 around the lateral side 2.53 and to substantially the midportion of the posterior side 2.57 thereof (i.e., along the posterior/lateral quadrant, the lateral side, and the anterior/lateral quadrant of the upper surface 2.47 of the base member 2.43. The ends of the medial ledge 2.63 and the lateral ledge 2.64 at the anterior side 2.55 of the base member 2.43 may be joined together so that the medial and lateral ledges 2.63, 2.64 form a single, continuous ledge from the posterior/lateral quadrant around the anterior side 2.55 to the posterior/medial quadrant as clearly shown in FIG. 25. While the base member 2.43 is not shown in the drawings as including a lateral fin similar to the lateral fin 65 of the base member 43, such a lateral fin could be included if desired.

The base member 2.43 may be constructed in various manners and out of various materials as will now be apparent to those skilled in the art. Thus, for example, the base member 2.43 can be machined or otherwise constructed in the same manner hereinabove described relative to the base member 43 and reference should be made to that disclosure for a full and complete understanding thereof.

The articular bearing member 2.45 has an upper or proximal surface 2.67 with a medial concavity 2.79 and a lateral concavity 2.81 for pivotally receiving and coacting with the face surfaces of the respective medial and lateral condylar portions 2.27, 2.29 of the femoral component 2.23, a lower or distal surface 2.69, a medial side 2.71, a lateral side 2.73, an anterior or front side 2.75, and a posterior or rear side 2.77, and is otherwise substantially similar to the articular bearing member 45. However, the articular bearing member 2.45 does not include in the lower surface 2.69 thereof corresponding to the slot 87 in the lower surface 69 of the articular bearing member 45.

The articular bearing member 2.45 preferably has a medial groove 2.89 similar to the medial groove 89 of the articular bearing member 2.45 for guidingly receiving the medial ledge 2.63 of the base member 2.43. Thus, the medial groove 2.89 preferably extends upward from the lower surface 2.69 thereof adjacent the medial side 2.71 thereof and extending generally from substantially the midportion of the anterior side 2.75 around the medial side 2.71 and to substantially the midportion of the posterior side 2.77 thereof (i.e., along the posterior/medial quadrant, the medial side, and the anterior/medial quadrant of the lower surface 2.69 of the articular bearing member 2.45). In addition, the articular bearing member 2.45 preferably includes a lateral groove 2.91 for guidingly receiving the medial ledge 2.64 of the base member 2.43. The lateral groove 2.91 preferably extends upward from the lower surface 2.69 thereof adjacent the lateral side 2.73 thereof and extending generally from substantially the midportion of the anterior side 2.75 around the lateral side 2.73 and to substantially the midportion of the posterior side 2.77 thereof (i.e., along the posterior/lateral quadrant, the lateral side, and the anterior/lateral quadrant of the lower surface 2.69 of the articular bearing member 2.45). The ends of the medial groove 2.89 and the lateral groove 2.91 preferably met at the midportion of the anterior side 2.75 of the articular bearing member 2.45 so that the medial and lateral grooves 2.89, 2.91 form a single, continuous groove from the posterior/lateral quadrant around the anterior side 2.75 to the posterior/medial quadrant as clearly shown in FIG. 26.

The articular bearing member 2.45 may be constructed in various manners and out of various materials as will now be apparent to those skilled in the art. Thus, for example, the articular bearing member 2.45 can be machined or otherwise constructed in the same manner hereinabove described relative to the articular bearing member 45 and reference should be made to that disclosure for a full and complete understanding thereof.

The tibial component 2.25 includes restriction means for restricting the slidable movement of the articular bearing member 2.45 relative to the base member 2.43 to allow a swinging motion of the lateral portion of the upper surface 2.67 of the articular bearing member 2.45 and a pivotal motion of the medial portion of the upper surface 2.67 of the articular bearing member 2.45. The restriction means may be designed to restrict the pivoting motion of the articular bearing member 2.45 to approximately 20 degrees of internal/external rotation of the knee joint 13 as will now be apparent to those skilled in the art. The restriction means may be constructed or formed by various structure. Preferably, however, the restriction means is formed or defined by the coaction of the medial and lateral ledges 2.63, 2.64 the base member 2.43 with the medial and lateral grooves 2.89, 2.91 of the articular bearing member 2.45. This design allows a general swinging motion of the lateral portion of the articular bearing member 2.45 anteriorly and posteriorly while the medial portion of the articular bearing member 2.45, although permitted some translational movement with respect to the base member 42.3, is more stationary.

The method of replacing a knee joint 13 using the joint prosthesis 2.11 is substantially the same as hereinabove described relative to the joint prosthesis 11, and reference should be made to that disclosure for a full and complete understanding thereof.

A third preferred embodiment of the knee prosthesis of the present invention is shown generally in FIGS. 30–40 and identified by the numeral 3.11. The knee prosthesis 3.11 is also designed to replace at least a portion of a knee joint 13 between the distal end 17 of a femur 15 and the proximal end 21 of a tibial 19.

The knee prosthesis 3.11 includes a femoral component 3.23 for mounting to the distal end 17 of the femur 15, and a tibial component 3.25 for mounting to the proximal end 21 of the tibia 19 and for articulating with the femoral component 3.23.

The femoral component 3.23 may be identical to the femoral component 23 and includes, in general, a medial condylar portion 3.27, a lateral condylar portion 3.29, and a patellar flange portion 3.31. Reference should be made to the above disclosure of the femoral component 23 for a complete and thorough understanding of the construction and function of the femoral component 3.23.

The tibial component 3.25 is preferably similar to the tibial component 25 and includes a base or tray member 3.43 for being secured to the proximal end 21 of the tibia 19, and an articular bearing, insert or superstructure member 3.45 for being fixedly mounted on the base member 3.43.

The base member 3.43 preferably includes a head portion 3.46 and attachment aids 3.59 for helping to secure the head portion 3.46 to the proximal end 21 of the tibia 19. The attachment aids 3.59 may include one or more pegs, fins, screws, surface treatments, etc., on the lower surface of the head portion 3.46 as will now be apparent to those skilled in the art. In addition, the upper surface of the head portion 3.46 may include articular bearing attachment aids (not shown) for helping to fixedly secure the articular bearing member 3.45 to the base member 3.43. Such articular bearing attachment aids may include one or more undercut flanges extending upward from the upper surface of the head portion 3.46 for coacting with coacting grooves in the lower surface of the articular bearing 3.45 such as disclosed at column 2, lines 46–52 of Lacey, U.S. Pat. No. 4,759,767, issued Jul. 26, 1988, incorporated herein by reference.

The base member 3.43 may be constructed in various manners and out of various materials as will now be apparent to those skilled in the art. Thus, for example, the base member 3.43 can be machined or otherwise constructed in the same manner hereinabove described relative to the base member 43 and reference should be made to that disclosure for a full and complete understanding thereof.

The articular bearing member 3.45 has an upper or proximal surface 3.67 with a medial concavity 3.79 and a lateral concavity 3.81 for pivotally receiving and coacting with the face surfaces of the respective medial and lateral condylar portions 3.27, 3.29 of the femoral component 3.23, and a lower or distal surface for being fixedly secure to the upper surface of the head portion 3.46 of the base member 3.43 as described above.

Figure 32:
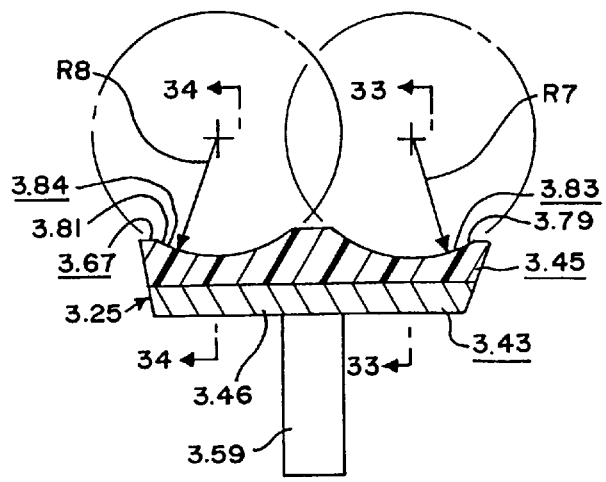
FIG. 32 is a sectional view substantially as taken on line 32—32 of FIG. 31, with portions thereof omitted for clarity.
Figure 33:
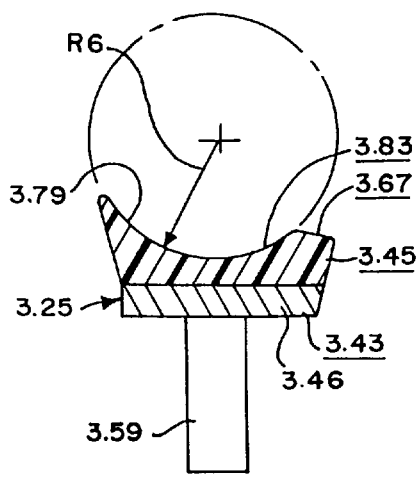
FIG. 33 is a sectional view substantially as taken on line 33—33 of FIG. 32, with portions thereof omitted for clarity.
Figure 35:
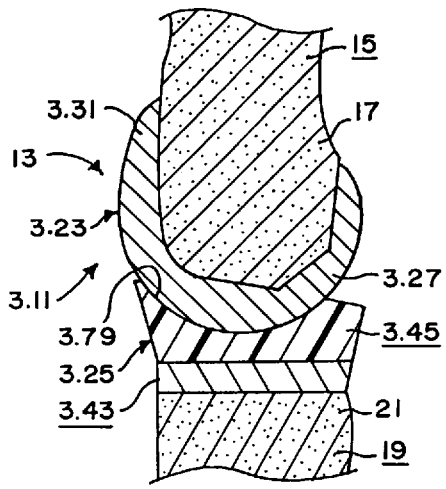
FIG. 35 is a somewhat diagrammatic medial sagittal sectional view of the knee prosthesis of FIG. 30, shown implanted in a knee joint with the knee joint substantially fully extended.
Figure 37:
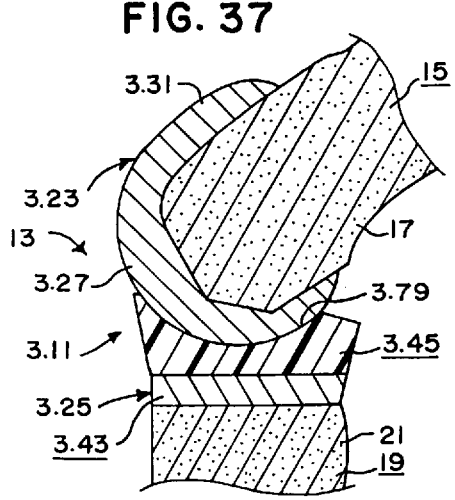
FIG. 37 is similar to FIG. 35 but shows the knee joint partially flexed.

The medial concavity 3.79 is preferably identical to the medial concavity 79 of the upper surface 67 of the articular bearing member 45 and has a face surface 3.83 for articulatingly receiving a portion of the face surface of the medial condylar portion 3.27 of the femoral component 3.23 with the face surface 3.83 preferably defined by a precise proximal sagittal curvature formed by the radius R6 shown in FIG. 33, and a precise proximal coronal curvature formed by the radius R7 shown in FIG. 32. The radius R6 is preferably the same size as the radius R7 so that the face surface 3.83 forms a semispherical shape. In addition, the radii R6, R7 are preferably substantially congruent with or approximately the same size as the radii R1, R2, with appropriate clearances, so that there is substantially complete surface-to-surface contact between the face surface of the medial condylar portion 3.27 of the femoral component 3.23 and the face surface 3.83 of the medial concavity 3.79 of the articular bearing member 3.45 of the tibial component 3.25 throughout a significant portion of the range of flexion of the knee joint 13, for example, between full extension of the knee joint 13 as shown in FIG. 35 and approximately 60° of flexion of the knee joint 13 as illustrated in FIG. 37.

Figure 31:
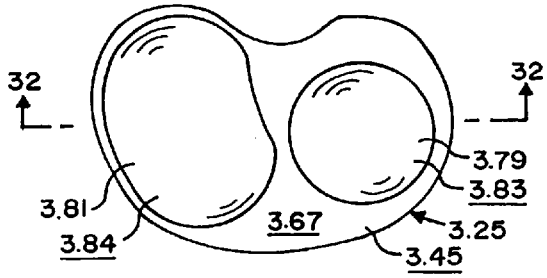
FIG. 31 is a top plan view of the tibial component of the knee prosthesis of FIG. 30.
Figure 34:
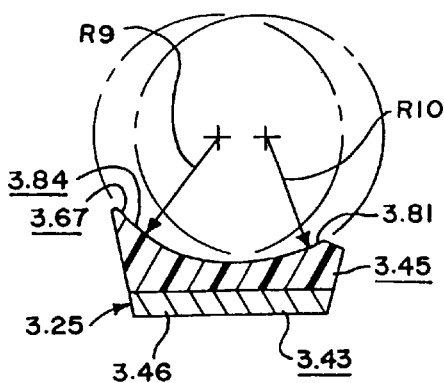
FIG. 34 is a sectional view substantially as taken on line 34—34 of FIG. 32, with portions thereof omitted for clarity.
Figure 36:
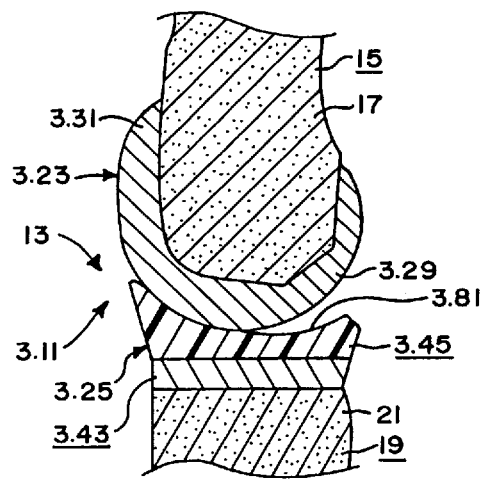
FIG. 36 is a somewhat diagrammatic lateral sagittal sectional view of the knee prosthesis of FIG. 30, shown implanted in a knee joint with the knee joint substantially fully extended.
Figure 38:
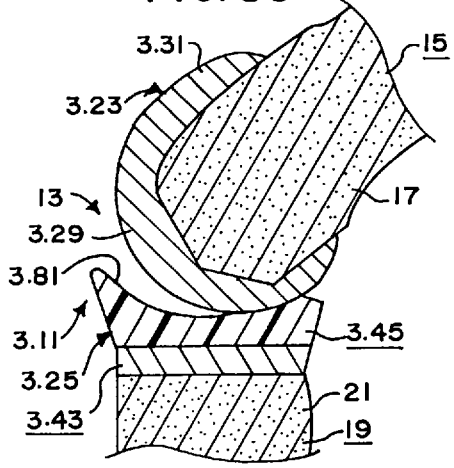
FIG. 38 is similar to FIG. 36 but shows the knee joint partially flexed.
Figure 39:
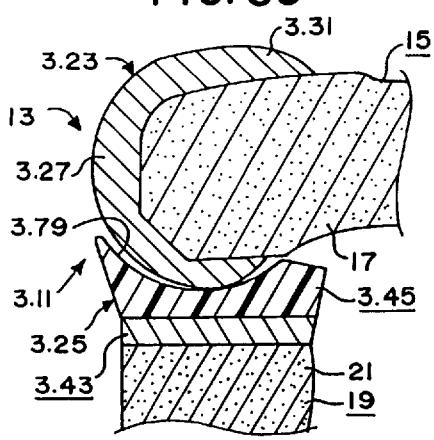
FIG. 39 is similar to FIG. 35 but shows the knee joint flexed substantially 90 degrees.
Figure 40:
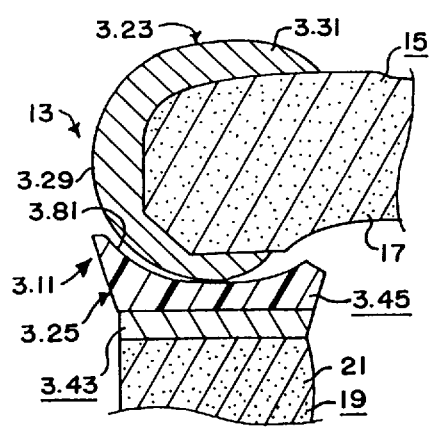
FIG. 40 is similar to FIG. 36 but shows the knee joint flexed substantially 90 degrees.

The lateral concavity 3.81 has a face surface 3.84 for articulatingly receiving a portion of the face surface of the lateral condylar portion 3.29 of the femoral component 3.23 with the face surface 3.84 preferably defined by a precise proximal coronal curvature formed by the radius R8 shown in FIG. 32, a precise anterior sagittal curvature formed by the radius R9 shown in FIG. 34, and a precise posterior sagittal curvature formed by the radius R10 shown in FIG. 34. The radii R8, R9, R10 are preferably substantially congruent with or approximately the same size as the radii R1, R2, with appropriate clearances, so that there is substantial surface-to-surface contact between the face surface of the lateral condylar portion 3.29 of the femoral component 3.23 and the anterior end of the face surface 3.84 of the lateral concavity 3.81 of the articular bearing member 3.45 of the tibial component 3.25 during full extension of the knee joint 13 as shown in FIG. 36 and between the face surface of the lateral condylar portion 3.29 of the femoral component 3.23 and the posterior end of the face surface 3.84 of the lateral concavity 3.81 of the articular bearing member 3.45 of the tibial component 3.25 during partial extension or extension of the knee joint 13 as shown in FIG. 38. The lateral concavity 3.81 is preferably curved about an axis extending generally perpendicular to the center of the medial concavity 3.79 when viewed in plan as shown in FIG. 31 so that flexion of the knee joint 13 will cause both the medial condylar portion 3.27 and the lateral condylar portion 3.29 to pivot about that axis as will now be apparent to those skilled in the art.

The articular bearing member 3.45 may be constructed in various manners and out of various materials as will now be apparent to those skilled in the art. Thus, for example, the articular bearing member 3.45 can be machined or otherwise constructed in the same manner hereinabove described relative to the articular bearing member 45 and reference should be made to that disclosure for a full and complete understanding thereof.

The method of replacing a knee joint 13 using the joint prosthesis 3.11 is substantially the same as hereinabove described relative to the joint prosthesis 11, and reference should be made to that disclosure for a full and complete understanding thereof.

A fourth preferred embodiment of the knee prosthesis of the present invention is shown generally in FIGS. 30–40 and identified by the numeral 4.11. The knee prosthesis 4.11 is also designed to replace at least a portion of a knee joint 13 between the distal end 17 of a femur 15 and the proximal end 21 of a tibial 19.

The knee prosthesis 4.11 includes a femoral component 4.23 for mounting to the distal end 17 of the femur 15, and a tibial component 4.25 for mounting to the proximal end 21 of the tibia 19 and for articulating with the femoral component 4.23.

The femoral component 4.23 may be identical to the femoral component 23 and includes, in general, a medial condylar portion 4.27, a lateral condylar portion 4.29, and a patellar flange portion 4.31. Reference should be made to the above disclosure of the femoral component 23 for a complete and thorough understanding of the construction and function of the femoral component 4.23.

Figure 41:
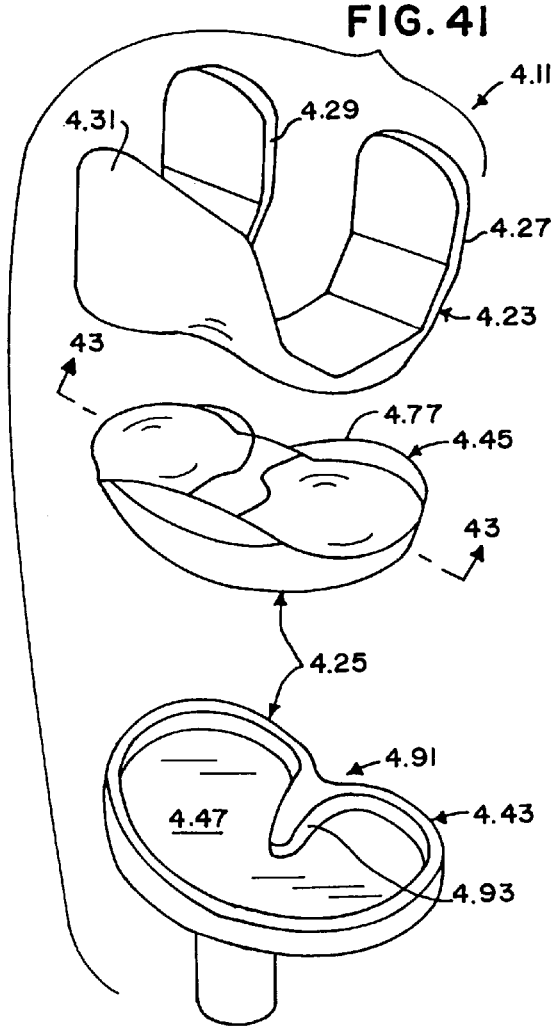
FIG. 41 is an exploded perspective view of a right knee prosthesis, illustrating a fourth preferred embodiment of the present invention, the left knee prosthesis being a substantial mirror image thereof.
Figure 42:
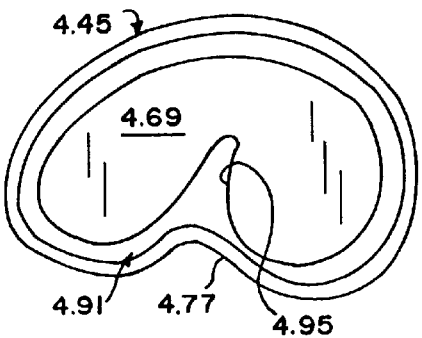
FIG. 42 is a top plan view of a base member of the tibial component of the knee prosthesis of FIG. 41.
Figure 43:
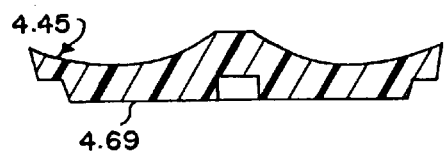
FIG. 43 is a sectional view substantially as taken on line 43—43 of FIG. 41, with portions thereof omitted for clarity.
Figure 44:
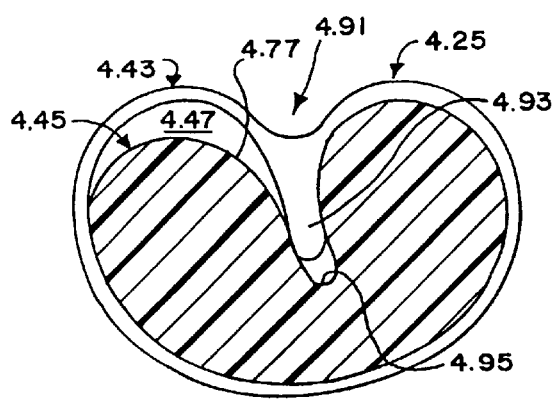
FIG. 44 is a somewhat diagrammatic sectional view similar to FIGS. 23 and 28 but showing the articular bearing member of the tibial component of the knee prosthesis of FIG. 41 substantially fully rotated in an anterior direction with respect to the base member of the tibial component, and with portions omitted for clarity.
Figure 45:
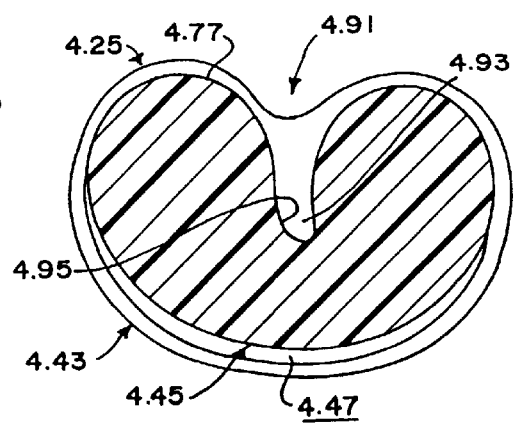
FIG. 45 is a somewhat diagrammatic sectional view similar to FIGS. 24 and 29 but showing the articular bearing member of the tibial component of the knee prosthesis of FIG. 41 substantially fully rotated in a posterior direction with respect to the base member of the tibial component, and with portions omitted for clarity.
Figure 51:
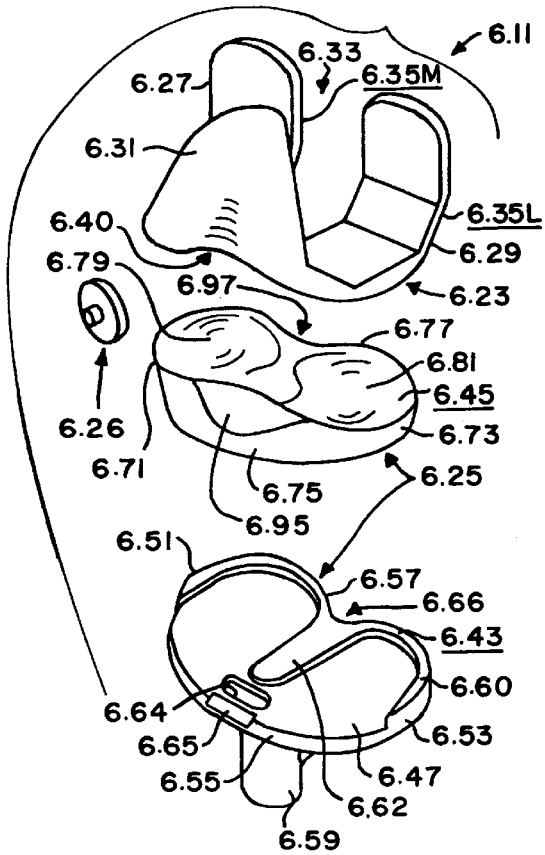
FIG. 51 is an exploded perspective view of a left knee prosthesis, illustrating a sixth preferred embodiment of the present invention, the right knee prosthesis being a substantial mirror image thereof.

The tibial component 4.25 is preferably substantially similar to the tibial component 2.25 and includes a base or tray member 4.43 for being secured to the proximal end 21 of the tibia 19, and an articular bearing, insert or superstructure member 4.45 for being movably mounted on the base member 4.43. The base member 4.43 and articular bearing member 4.45 are substantially similar to the base member 2.43 and articular bearing member 2.45 of the tibial component 2.25 and reference should be made to the above disclosure of the base member 2.43 and articular bearing member 2.45 for a complete and thorough understanding of the construction and function of the base member 4.43 and articular bearing member 4.45. However, the tibial component 4.25 further includes guide means 4.91 for guiding the movement of the articular bearing member 4.45 on the base member 4.43. More specifically, the guide means 4.91 preferably includes a guide finger 4.93 on the upper surface 4.47 of the base member 4.43 and extending inwardly from the medial ledge 4.63 as clearly shown in FIG. 41, and a guide groove 4.95 in the lower surface 4.69 of the articular bearing member 4.45 and extending inwardly from the posterior side 4.77 thereof as clearly shown in FIG. 42 for receiving and coacting with the guide finger 4.93 to cause the articular bearing member 4.45 to pivot about one or more axes extending generally perpendicular to the medial portion of the upper surface 4.47 of the articular bearing member 4.45.

The base member 4.43 may be constructed in various manners and out of various materials as will now be apparent to those skilled in the art. Thus, for example, the base member 4.43 can be machined or otherwise constructed in the same manner hereinabove described relative to the base member 43 and reference should be made to that disclosure for a full and complete understanding thereof.

The articular bearing member 4.45 may be constructed in various manners and out of various materials as will now be apparent to those skilled in the art. Thus, for example, the articular bearing member 4.45 can be machined or otherwise constructed in the same manner hereinabove described relative to the articular bearing member 45 and reference should be made to that disclosure for a full and complete understanding thereof.

The method of replacing a knee joint 13 using the joint prosthesis 4.11 is substantially the same as hereinabove described relative to the joint prosthesis 11, and reference should be made to that disclosure for a full and complete understanding thereof.

A fifth preferred embodiment of the knee prosthesis of the present invention is shown generally in FIGS. 46–50 and identified by the numeral 5.11. The knee prosthesis 5.11 is also designed to replace at least a portion of a knee joint 13 between the distal end 17 of a femur 15 and the proximal end 21 of a tibial 19.

The knee prosthesis 5.11 includes a femoral component 5.23 for mounting to the distal end 17 of the femur 15, and a tibial component 5.25 for mounting to the proximal end 21 of the tibia 19 and for articulating with the femoral component 5.23.

The femoral component 5.23 may be identical to the femoral component 23 and includes, in general, a medial condylar portion 5.27, a lateral condylar portion 5.29, and a patellar flange portion 5.31. Reference should be made to the above disclosure of the femoral component 23 for a complete and thorough understanding of the construction and function of the femoral component 5.23.

The tibial component 5.25 includes a base or tray member 5.43 for being secured to the proximal end 21 of the tibia 19, and an articular bearing, insert or superstructure member 5.45 for being mounted on the base member 5.43. The base member 5.43 and articular bearing member 5.45 are substantially similar to the base member 2.43 and articular bearing member 2.45 of the tibial component 2.25 and reference should be made to the above disclosure of the base member 2.43 and articular bearing member 2.45 for a complete and thorough understanding of the construction and function of the base member 5.43 and articular bearing member 5.45. However, the articular bearing member 5.45 is divided into a separate medial articular bearing, insert or superstructure member 5.45M for being fixedly mounted on the base member 5.43, and a separate lateral articular bearing, insert or superstructure member 5.45L for being movably mounted on the base member 5.43. Also, because the medial articular bearing member 5.45M is fixedly mounted on the base member 5.43, the medial ledge may be omitted.

The base member 5.43 may be constructed in various manners and out of various materials as will now be apparent to those skilled in the art. Thus, for example, the base member 5.43 can be machined or otherwise constructed in the same manner hereinabove described relative to the base member 43 and reference should be made to that disclosure for a full and complete understanding thereof.

The medial articular bearing member 5.45M may be similar to the medial side of the articular bearing 45 of the tibial component 25, and may have an upper or proximal surface 5.67M with a medial concavity 5.79M for pivotally receiving and coacting with the face surfaces of the medial condylar portion 5.27 of the femoral component 5.23, and a lower or distal surface 5.69M for being fixedly attached to the medial side of the upper surface 5.47 of the base member 5.43 in any manner now apparent to those skilled in the art such as, for example, by way of articular bearing attachment aids such as one or more coacting groove and flange structures such as hereinabove disclosed relative to the knee prosthesis 3.11 as will now be apparent to those skilled in the art.

The lateral articular bearing member 5.45L may be similar to the lateral side of the articular bearing 45 of the tibial component 25, and may have and upper or proximal surface 5.67L with a lateral concavity 5.79L for pivotally receiving and coacting with the face surfaces of the lateral condylar portion 5.29 of the femoral component 5.23, and a lower or distal surface 5.69L for being movably positioned on the lateral side of the upper surface 5.47 of the base member 5.43 as will now be apparent to those skilled in the art. The lateral articular bearing member 5.45L will coact with the lateral ledge 5.64 of the base member 5.43 to form or define a restriction means for allowing allows a general swinging motion of the lateral portion of the lateral articular bearing member 5.45L, while the medial articular bearing member 5.45M remains fixed and stationary.

The articular bearing members 5.45M, 5.45L may be constructed in various manners and out of various materials as will now be apparent to those skilled in the art. Thus, for example, the articular bearing members 5.45M, 5.45L can be machined or otherwise constructed in substantially the same manner hereinabove described relative to the articular bearing member 45 and reference should be made to that disclosure for a full and complete understanding thereof.

The method of replacing a knee joint 13 using the joint prosthesis 5.11 is substantially the same as hereinabove described relative to the joint prosthesis 11, and reference should be made to that disclosure for a full and complete understanding thereof.

A sixth preferred embodiment of the knee prosthesis of the present invention is shown generally in FIGS. 51–76 and identified by the numeral 6.11. The knee prosthesis 6.11 is also designed to replace at least a portion of a knee joint 13 between the distal end 17 of a femur 15 and the proximal end 21 of a tibial 19.

The knee prosthesis 6.11 includes a femoral component 6.23 for mounting to the distal end 17 of the femur 15, a tibial component 6.25 for mounting to the proximal end 21 of the tibia 19 and for articulating with the femoral component 6.23, and may, when desired, include a patellar component 6.26 for mounting to the posterior side of the patella 22 of the knee joint 13 and for articulating with the femoral component 6.23.

The femoral component 6.23 is similar to the femoral component 23 and includes, in general, a medial condylar portion 6.27, a lateral condylar portion 6.29, and a patellar flange portion 6.31 joining the anterior ends of the medial and lateral condylar portions 6.27, 6.29 together with the medial and lateral condylar portions 6.27, 6.29 substantially parallel to and spaced apart from one another to form an intercondylar notch or recess 6.33 therebetween as clearly shown in the drawings. The medial and lateral condylar portions 6.27, 6.29 have medial and lateral outer or face surfaces 6.35M, 6.35L, respectively, for articulatingly engaging a portion of the tibial component 6.25 as will hereinafter become apparent.

The face surface 6.35M of the medial condylar portion 6.27 preferably has a small indentation 6.36 therein to accommodate a relatively high anterior medial lip of the tibial insert member 6.45 of the tibial component 6.25 to prevent anterior femoral dislocation as will hereinafter become apparent. The face surface 6.35L of the lateral condylar portion 6.29 may also have a small indentation (not shown) therein to accommodate a relatively high anterior lateral lip of the tibial insert member 6.45 of the tibial component 6.25 to prevent anterior femoral dislocation as will hereinafter become apparent.

Figure 55:
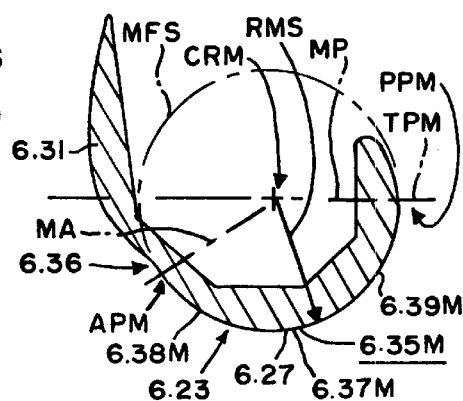
FIG. 55 is a sectional view substantially as taken on line 55—55 of FIG. 54, with portions thereof omitted for clarity.

The medial face surface 6.35M has a distal side or end 6.37M, an anterior side 6.38M, a posterior side 6.39M, and a curvature defined by a single radius of curvature RMS in the sagittal plane from a posterior point PPM on the posterior side 6.39M on a transverse plane TPM passing through the center CRM of the single radius of curvature RMS to an anterior point APM on the anterior side 6.38M, for example, about 130° from the posterior point PPM, as clearly illustrated in FIG. 55. It should be noted that the single radius of curvature RMS could, if desired, extend from the anterior point APM fully and completely to the end of the posterior side 6.39M of the medial face surface 6.35M, rather than stopping at the posterior point PPM as shown in FIG. 55 (i.e., rather than having a "closing radius" that is smaller than the single radius of curvature RMS as shown in FIG. 55, the "closing radius" could be formed as merely a continuation of the single radius of curvature RMS as will now be apparent to those skilled in the art).

Figure 56:
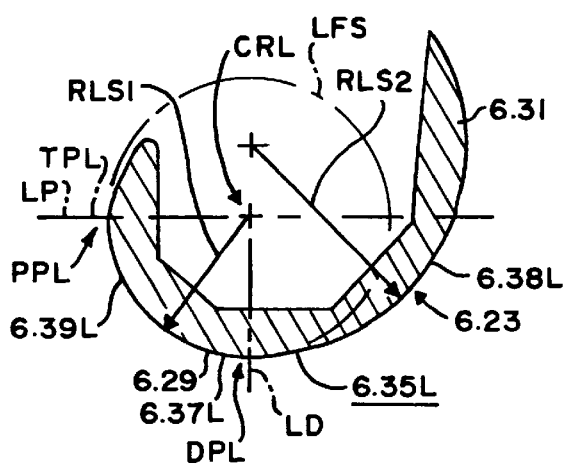
FIG. 56 is a sectional view substantially as taken on line 56—56 of FIG. 54, with portions thereof omitted for clarity.
Figure 57:
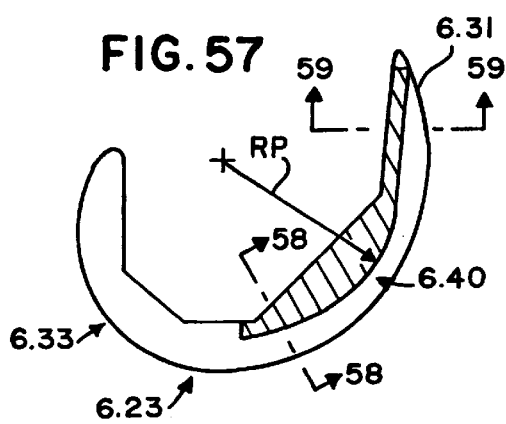
FIG. 57 is a sectional view substantially as taken on line 57—57 of FIG. 54, with portions thereof omitted for clarity.
Figure 58:
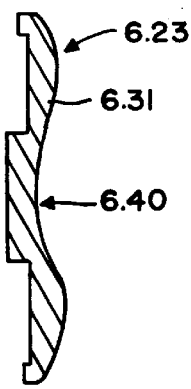
FIG. 58 is a sectional view substantially as taken on line 58—58 of FIG. 57, with portions thereof omitted for clarity.
Figure 59:
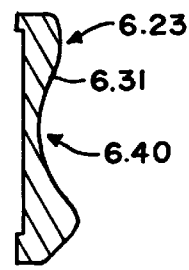
FIG. 59 is a sectional view substantially as taken on line 59—59 of FIG. 57, with portions thereof omitted for clarity.
Figure 60:
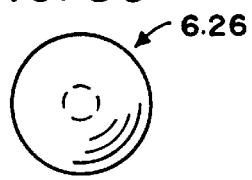
FIG. 60 is an articular side or elevation view of a patellar component of the knee prosthesis of FIG. 51.
Figure 61:
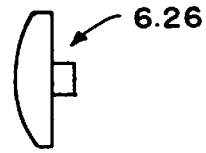
FIG. 61 is a side elevational view of the patellar component of FIG. 60.
Figure 62:
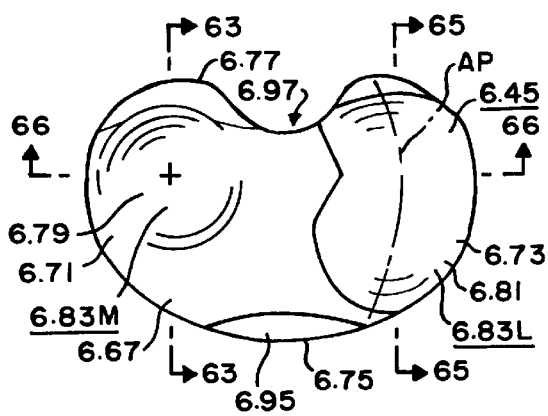
FIG. 62 is a top plan view of an articular bearing of a tibial component of the knee prosthesis of FIG. 51.
Figure 63:
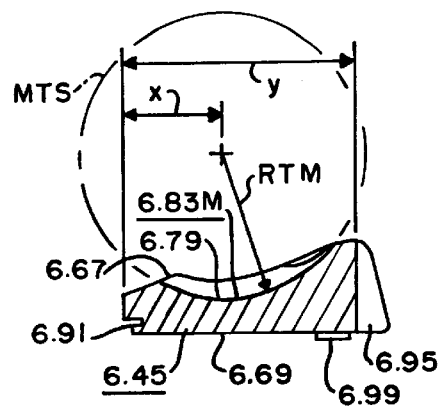
FIG. 63 is a sectional view substantially as taken on line 63—63 of FIG. 62, with portions thereof omitted for clarity.
Figure 64:
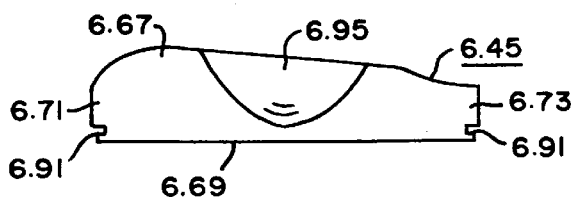
FIG. 64 is a front or anterior elevational view of the articular bearing of FIG. 62.

The lateral face surface 6.35L has a distal side or end 6.37L, an anterior side 6.38L, a posterior side 6.39L, and a curvature defined by a single radius of curvature RLS1 in the sagittal plane from a posterior point PPL on the posterior side 6.39L on a transverse plane TPL passing through the center CRL of the single radius of curvature RLS1 to a distal point DPL on the distal side 6.37L, for example about 90° from the posterior point PPL, as clearly illustrated in FIG. 56. It should be noted that the single radius of curvature RLS1 could, if desired, extend, for example, 130° or so from the posterior point PPL, similar to the single radius of curvature RMS of the medial face surface 6.35M. In addition, it should be noted that the single radius of curvature RLS1 could, if desired, extend from the posterior point PPL fully and completely to the end of the posterior side 6.39L of the lateral face surface 6.35L, rather than stopping at the posterior point PPL as shown in FIG. 56 (i.e., rather than having a "closing radius" that is smaller than the single radius of curvature RLS1 as shown in FIG. 56, the "closing radius" could be formed as merely a continuation of the single radius of curvature RLS1 as will now be apparent to those skilled in the art).

Figure 53:
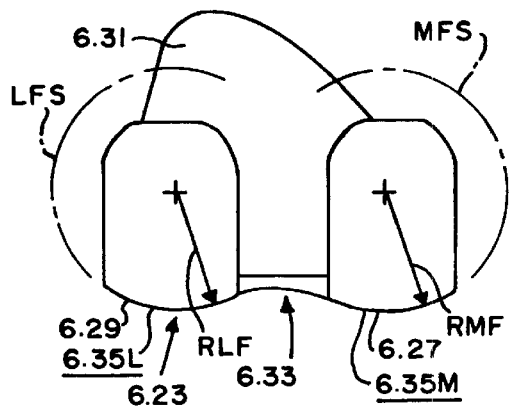
FIG. 53 is a rear or posterior elevational view of the femoral component of FIG. 52.
Figure 54:
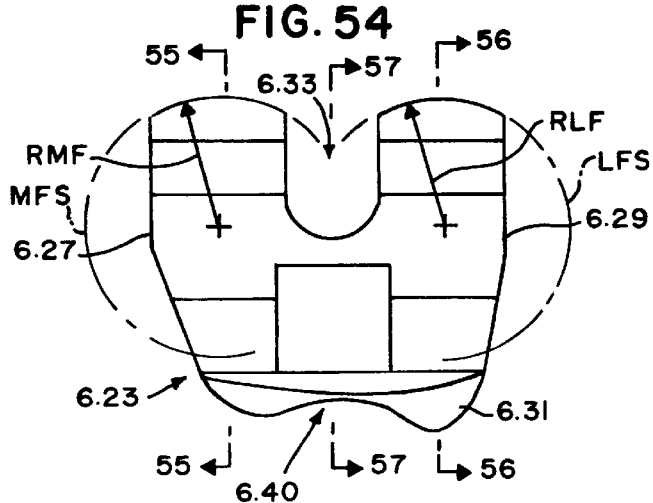
FIG. 54 is a top plan view of the femoral component of FIG. 52.

The medial condylar portion 6.27 is at least partially semispherical. That is, the medial distal side 6.37M and medial posterior side 6.39M of the face surface 6.35M may be defined, at least in part, by precise sagittal and coronal curvatures formed by the radius RMS in the sagittal plane as shown in FIG. 55, and by a radius RMF in the frontal, or coronal, plane as shown in FIGS. 54 and 53, with the radii RMS, RMF being the same dimension in both the sagittal and frontal, or coronal, planes, so that the medial distal side 6.37M and medial posterior side 6.39M of the face surface 6.35M form a medial sphere or spherical portion as indicated by the broken line circle MFS in FIGS. 53–55, and have a single radius of curvature from, for example, approximately 40° of hyperextension as illustrated by the medial-anterior or hyperextension plane MA in FIG. 55 to, for example, approximately 90° of flexion as illustrated by the medial-posterior or flexion plane MP in FIG. 55. As shown in FIG. 55, the medial-posterior or flexion plane MP may be aligned and congruent with the transverse plane TPM. Also, the single radius of curvature in the sagittal plane could, alternatively, extend beyond 90° of flexion to retain femorotibial congruency and high contact area to reduce polyethylene stress.

The lateral condylar portion 6.29 is also at least partially semispherical. That is, the lateral posterior side 6.39L and at least a posterior portion of the lateral distal side 6.37L of the face surface 6.35L may be defined, in part, by precise sagittal and coronal, or frontal, curvatures formed by the radius RLS1 in the sagittal plane as shown in FIG. 56, and by a radius RLF in the frontal, or coronal, plane as shown in FIGS. 54 and 53, with the radii RLS1, RLF being the same dimension in both the sagittal and frontal, or coronal, planes, so that the lateral posterior side 6.39L and lateral distal side 6.37L of the face surface 6.35L form a lateral sphere or spherical portion as indicated by the broken line circle LFS in FIGS. 53, 54 and 56, and have a single radius of curvature from, for example, approximately 0° of extension as illustrated by the lateral-distal or extension plane LD in FIG. 56 (or from approximately 40° of hyperextension in the medial-anterior or hyperextension plane when the face surface 6.35L of the lateral condylar portion 6.29 is provided with a small indentation similar to the indentation 6.36 in the face surface 6.35M of the medial condylar portion 6.27) to, for example, approximately 90° of flexion as illustrated by the lateral-posterior or flexion plane LP in FIG. 56. Alternatively, this single radius of curvature in the sagittal plane could also extend beyond 90° of flexion to retain femorotibial congruency and high contact area to reduce polyethylene stress. As shown in FIG. 56, the lateral-posterior or flexion plane LP may be aligned and congruent with the transverse plane TPL. The radii RLS1, RLF may be the same dimension as the radii RMS, RMF, so that the lateral femoral sphere or spherical portion LFS has the same size and curvature as the medial femoral sphere or spherical portion MFS. However, it is not essential for the present invention that the lateral femoral sphere or spherical portion LFS be the same size and curvature as the medial femoral sphere or spherical portion MFS. The anterior side 6.38L and at least an anterior portion of the distal side 6.37L of the face surface 6.35L may be defined, at least in part, by precise sagittal and coronal, or frontal, curvatures formed by a second radius RLS2 in the sagittal plane as shown in FIG. 56, and by the radius RLF in the frontal, or coronal, plane as shown in FIGS. 54 and 53.

Figure 52:
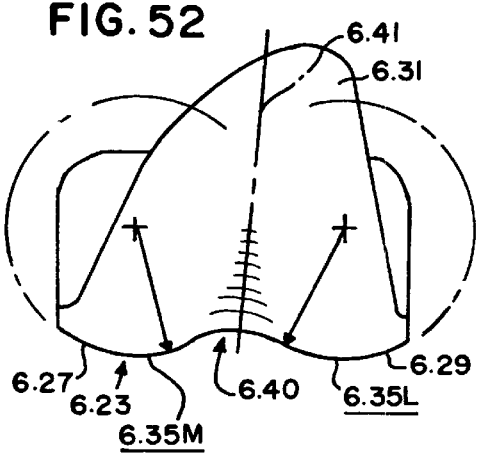
FIG. 52 is a front or anterior elevational view of a femoral component of the knee prosthesis of FIG. 51.

The patellar flange portion 6.31 may be asymmetric as clearly shown in FIG. 52, or may be symmetric as will now be apparent to those skilled in the art. The femoral component 6.23 preferably has a patellar groove 6.40 in the posterior or face surface of the patellar flange portion 6.31 and extending posteriorly to the intercondylar notch 6.33 to enable contact with the patellar component 6.26, or an unresurfaced patella, to at least 100° of flexion as will hereinafter become apparent. The patellar groove 6.40 is preferably centrally placed between the medial and lateral condyle portions 6.27, 6.29 at the beginning of the intercondylar notch 6.33 and then extends laterally at a 3.6° angle as indicated by the longitudinal axis 6.41 in FIG. 52. Alternatively, the patellar groove could be asymmetrically placed laterally with angulation between, for example, 0° and 10°. The patellar groove 6.40 preferably features a constant radius of curvature defined by a precise sagittal curvature formed by the radius RP shown in FIG. 57 to allow articulation of a highly congruent patellar implant. Such congruency can be maintained throughout the flexion cycle in both the sagittal and frontal planes with a saddle shaped patellar design.

The femoral component 6.23 may include typical attachment aids for helping to secure the femoral component 6.23 to the distal end 6.17 of the femur 6.15, etc. Such attachment aids may include one or more pegs, fins, surface treatments, indentations, etc., as will now be apparent to those skilled in the art.

The femoral component 6.23 may be constructed in various manners and out of various materials as will now be apparent to those skilled in the art. Thus, for example, the femoral component 6.23 can be machined, cast, forged or otherwise constructed as a one-piece, integral unit out of a medical grade, physiologically acceptable metal such as a cobalt chromium alloy or the like, in various sizes to fit a range of typical patients, or may be custom-designed for a specific patient based on data provided by a surgeon after physical and radiography examination of the specific patient, etc.

The femoral component 6.23 has been specifically designed to articulate with either a traditional anterior/posterior lipped PCL sparing tibial insert, a medial pivot tibial insert, both of which assemble into and are stationary with a metal tibial base, a mobile bearing design which may include medial pivot features, or a posterior stabilized cam and spine type tibial component to yield a traditional PCL substitution design.

The tibial component 6.25 shown in FIGS. 51, 62–67, and 71–76 is similar to the tibial component 3.25 and includes a base or tray member 6.43 for being secured to the proximal end 21 of the tibia 19, and an articular bearing, insert or superstructure member 6.45 for being fixedly mounted on the base member 6.43.

The base member 6.43 has an upper or proximal surface 6.47, a lower or distal surface 6.49, a medial side 6.51, a lateral side 6.53, an anterior or front side 6.55, and a posterior or rear side 6.57, and is otherwise similar to the base member 43. The upper surface 6.47 may be substantially flat and planar as shown in the drawings. The base member 6.43 preferably includes attachment aids 6.59 for helping to secure the base member 6.43 to the proximal end 21 of the tibia 19. Such attachment aids 6.59 may include one or more stems, pegs, fins, screws, surface treatments, etc., on the lower surface 6.49 thereof as will now be apparent to those skilled in the art.

The base member 6.43 preferably includes peripheral ledge or wall 6.60 extending upward from the upper surface 6.47 thereof adjacent the medial, lateral and posterior sides 6.51, 6.53, 6.57 thereof and extending generally from substantially the midportion of the medial side 6.51, around the posterior side 6.57, to substantially the midportion of the lateral side 6.53 thereof (i.e., along the posterior/medial quadrant, the posterior side, and the posterior/lateral quadrant of the upper surface 6.47 of the base member 6.43), and a central dovetail 6.62 extending upward from the upper surface 6.47 thereof centrally of the medial and lateral sides 6.51, 6.53 thereof and extending generally from substantially the midportion of the posterior side 6.57 to a point slightly anteriorly of the opposite ends of the peripheral ledge 6.60. The base member 6.43 preferably has an anterior recess 6.64 in the upper surface 6.47 thereof directly anteriorly of the central dovetail 6.62, and may have a ramp 6.65 extending from the anterior side 6.55 to the anterior recess 6.64.

The base member 6.43 preferably has a PCL cutout 6.66 in the posterior side 6.57 thereof located substantially centrally of the medial and lateral sides 6.51, 6.53 thereof to coact with a PCL cutout of the articular bearing member 6.45 and to allow the PCL to be preserved, if desired.

The base member 6.43 may be constructed in various manners and out of various materials as will now be apparent to those skilled in the art. Thus, for example, the base member 6.43 can be machined or otherwise constructed in the same manner hereinabove described relative to the base member 43 and reference should be made to that disclosure for a full and complete understanding thereof.

The articular bearing member 6.45 has an upper or proximal surface 6.67, a lower or distal surface 6.69, a medial side 6.71, a lateral side 6.73, an anterior or front side 6.75, and a posterior or rear side 6.77. The upper surface 6.67 of the articular bearing member 6.45 preferably has a medial concavity 6.79 for pivotally receiving and coacting with the face surface 6.35 of the medial condylar portion 6.27 of the femoral component 6.23, and a lateral concavity 6.81 for movably receiving and coacting with the face surface 6.35 of the lateral condylar portion 6.29 of the femoral component 6.23.

The medial concavity 6.79 has a face surface 6.83M for articulatingly receiving a portion of the face surface 6.35 of the medial condylar portion 6.27 of the femoral component 6.23. The medial concavity 6.79 is semispherical. That is, the face surface 6.83M of the concavity 6.79 is preferably defined by a precise proximal sagittal and coronal or frontal curvatures formed by the radius RTM shown in FIGS. 63 and 66, with the radius RTM being the same dimension in both the sagittal and frontal, or coronal, planes, so that the medial concavity 6.79 forms a medial sphere or spherical portion as indicated by the broken line circle MTS in FIGS. 63 and 66. The radius RTM is preferably substantially congruent with or approximately the same size and dimension as the radius RFM that defines the medial distal portion 6.37M and medial posterior portion 6.39M of the face surface 6.35 of the medial condylar portion 6.27 of the femoral component 6.23, with appropriate clearances, to create a ball and socket joint so that there is substantially complete surface-to-surface contact between the medial condylar portion 6.27 of the femoral component 6.23 and the medial concavity 6.79 of the tibial component 6.25 throughout the range of flexion of the knee joint 13. The spherical radius of the medial concavity 6.79 is preferably located in the posterior one third of the articular bearing member 6.45. That is, the centerpoint of the radius RTM is preferably located a distance X that is approximately one third of the overall depth Y of the articular bearing member 6.45 taken at the medial concavity 6.79 as clearly shown in FIG. 63. The anterior lip of the articular bearing member 6.45 adjacent the medial concavity 6.79 is preferably approximately almost four times taller than the posterior lip of the articular bearing member 6.45 adjacent the medial concavity 6.79 (for example, the anterior lip may be 11 millimeters tall and the posterior lip may be 3 millimeters tall) to provide adequate intrinsic stability comparable to a more traditional PCL substitution design, especially at flexion angles less than 90°.

Figure 65:
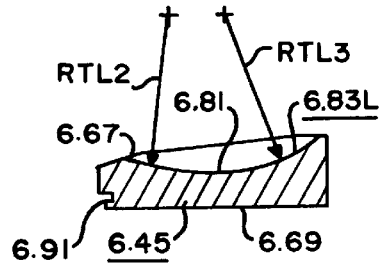
FIG. 65 is a sectional view substantially as taken on line 65—65 of FIG. 62, with portions thereof omitted for clarity.
Figure 66:
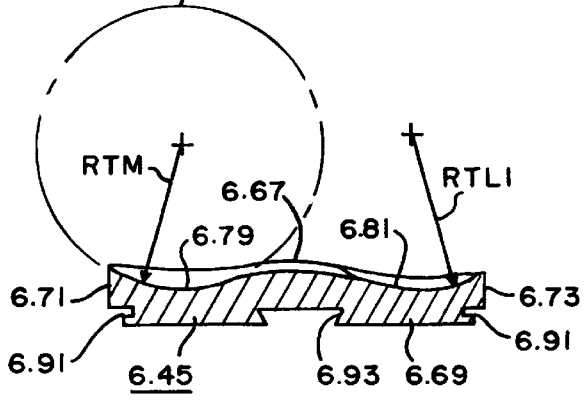
FIG. 66 is a sectional view substantially as taken on line 66—66 of FIG. 62, with portions thereof omitted for clarity.
Figure 67:
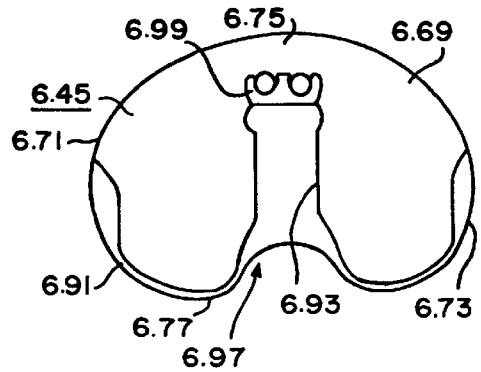
FIG. 67 is a bottom plan view of the articular bearing of FIG. 62.
Figure 68:
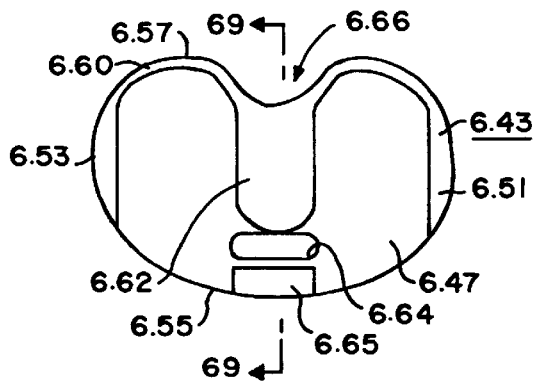
FIG. 68 is a top plan view of a base member of the tibial component of the knee prosthesis of FIG. 51.
Figure 69:
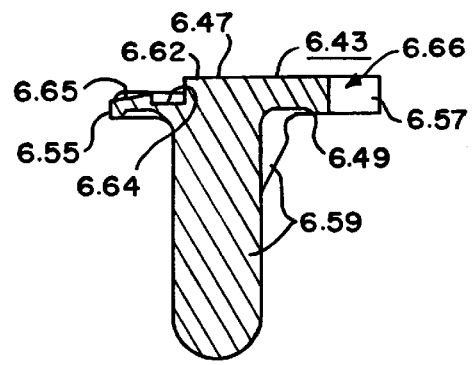
FIG. 69 is a sectional view substantially as taken on line 69—69 of FIG. 68, with portions thereof omitted for clarity.
Figure 70:
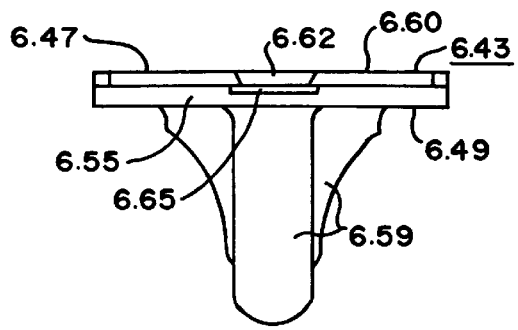
FIG. 70 is a front or anterior elevational view of the base member of FIG. 68.
Figure 71:
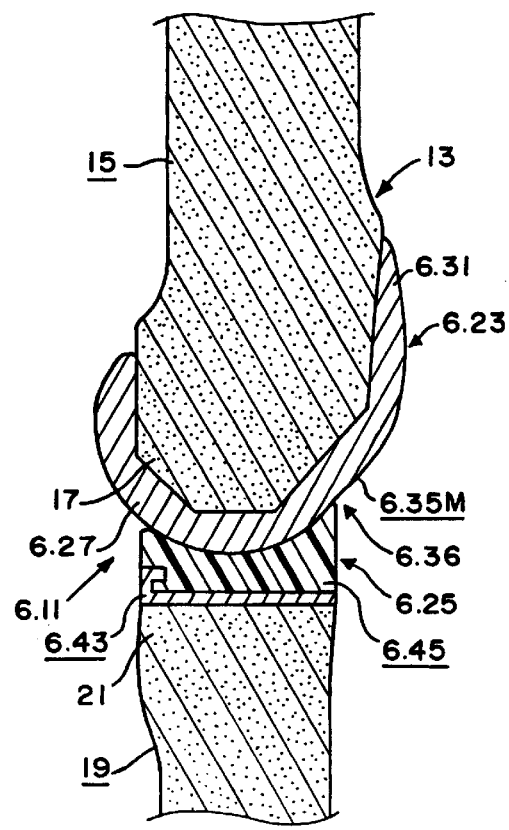
FIG. 71 is a somewhat diagrammatic sagittal sectional view of the femoral and tibial components of knee prosthesis of FIG. 51, taken substantially along the medial condyle of the femoral component and shown implanted in a knee joint with the knee joint substantially fully extended.
Figure 75:
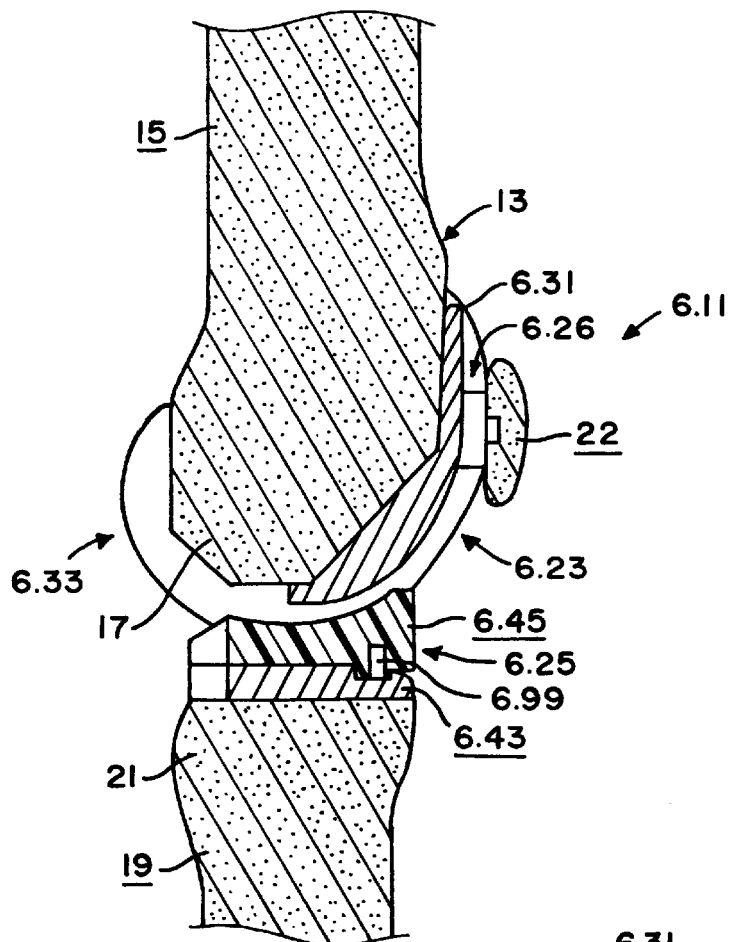
FIG. 75 is a somewhat diagrammatic sagittal sectional view of the femoral and tibial components of knee prosthesis of FIG. 51, taken substantially along the patellar groove of the femoral component and shown implanted in a knee joint with the knee joint substantially fully extended.
Figure 76:
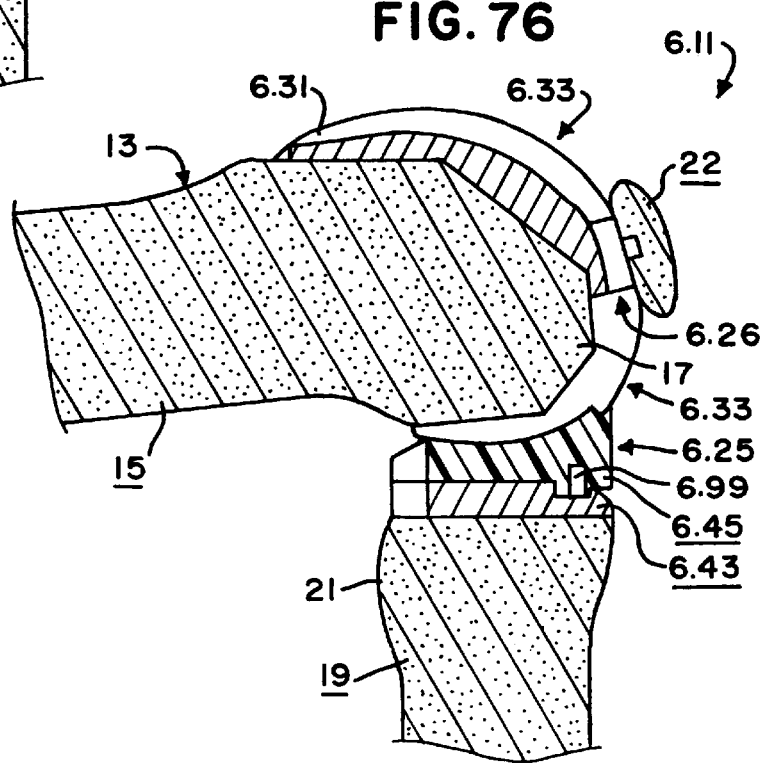
FIG. 76 is similar to FIG. 75 but shows the knee joint flexed substantially 100 degrees.

The lateral concavity 6.81 has a face surface 6.83L for articulatingly receiving a portion of the face surface 6.35 of the lateral condylar portion 6.29 of the femoral component 6.23. The face surface 6.83L of the concavity 6.81 is preferably defined by a precise proximal sagittal and coronal or frontal curvatures. The coronal or frontal curvature is formed by the radius RTL1 shown in FIG. 66, while the sagittal curvature is defined by a proximal radius RTL2, an anterior radius RTL3, and a tangent surface between the proximal and anterior radii RTL2, RTL3 as shown in FIG. 65, with the concavity 6.81 sweeping an arcuate path in the transverse plane as illustrated by the line AP in FIG. 62 allowing the tibia 19 to rotate 5° internally and 10° externally with respect to the femur 15 as the knee joint 13 is flexed and extended. This will prevent an edge loading condition with medial compartment liftoff, thereby significantly reducing edge loading on the lateral condyle.

The articular bearing member 6.45 preferably has a peripheral groove 6.91 adjacent the lower surface 6.69 thereof and extending generally from substantially the midportion of the medial side 6.71, around the posterior side 6.77, to substantially the midportion of the lateral side 6.73 thereof (i.e., along the posterior/medial quadrant, the posterior side, and the posterior/lateral quadrant of the lower surface 6.69 of the articular bearing member 6.45), and a central groove or slot 6.93 in the lower surface 6.69 thereof centrally of the medial and lateral sides 6.71, 6.73 thereof and extending generally from substantially the midportion of the posterior side 6.77 to a point slightly anteriorly of the opposite ends of the peripheral groove 6.91. The peripheral groove 6.91 and central groove 6.93 are specifically designed to coact with the peripheral ledge 6.60 and central dovetail 6.62 of the base member 6.43 to provide a front loading locking mechanism between the base member 6.43 and articular bearing member 6.45 to incorporate the benefits of both a peripheral capture and a centralized locking mechanism. The peripheral capture provided by the peripheral ledge 6.60 and peripheral groove 6.91 ensures conformity at the interface between the base and articular bearing members 6.43, 6.45, forming an integrated unit and minimizing micromotion between the base and articular bearing members 6.43, 6.45. The central interlock created by the central dovetail 6.62 and the central groove 6.93, provides enhanced engagement of the articular bearing member 6.45 and, combined with the peripheral capture, further reduces micromotion. By locating the leading or anterior edge of the central dovetail 6.62 slightly anteriorly of the opposite ends of the peripheral ledge 6.60, the central dovetail 6.62 initially engages the articular bearing member 6.45 to establish correct alignment before engagement of the peripheral capture, thereby facilitating easy assembly of the construct.

The articular bearing member 6.45 preferably has a gentle anterior radiused groove 6.95 in the anterior side 6.75 thereof located substantially centrally of the medial and lateral sides 6.71, 6.73 thereof to accommodate the patellar ligament to prevent impingement.

The articular bearing member 6.45 preferably has a PCL cutout 6.97 in the posterior side 6.77 thereof located substantially centrally of the medial and lateral sides 6.71, 6.73 thereof to coact with the PCL cutout 6.66 of the base member 6.43 and to allow the PCL to be preserved, if desired.

The articular bearing member 6.45 preferably includes a metal reinforced tab 6.99 on the distal surface 6.69 thereof for engaging the anterior recess 6.64 of the base member 6.43 to resist posterior-to-anterior shear forces at the femorotibial joint.

The articular bearing member 6.45 may be constructed in various manners and out of various materials as will now be apparent to those skilled in the art. Thus, for example, the articular bearing member 6.45 can be machined or otherwise constructed in the same manner hereinabove described relative to the articular bearing member 45 and reference should be made to that disclosure for a full and complete understanding thereof.

The method of replacing a knee joint 13 using the joint prosthesis 6.11 is substantially the same as hereinabove described relative to the joint prosthesis 11, and reference should be made to that disclosure for a full and complete understanding thereof.

As thus constructed and used, the present invention provides a joint prosthesis for a knee joint that includes a tibial component having a semispherical medial cavity and a lateral cavity; and a femoral component having a semispherical medial condylar portion for pivotally coacting with the semispherical medial cavity of the tibial component and a semispherical lateral condylar portion for movably coacting with the lateral cavity of the tibial component, with the semispherical medial condylar portion being substantially congruent with the semispherical medial cavity of the tibial component so that substantially complete surface-to-surface contact between the semispherical medial cavity of the tibial component and the semispherical medial condylar portion of the femoral component is provided throughout the range of flexion of the knee joint.

Although the present invention has been described and illustrated with respect to preferred embodiments thereof and a preferred use therefor, it is not to be so limited since modifications and changes can be made therein which are within the full intended scope of the invention.

We claim:

1. A knee prosthesis for replacing at least a portion of a knee joint between the distal end of a femur and the proximal end of a tibia; the knee prosthesis comprising:
   (a) a tibial component for mounting to the proximal end of the tibia, said tibial component including a proximal surface having a semispherical medial cavity and a lateral cavity; and
   (b) a femoral component for mounting to the distal end of the femur, said femoral component including a medial condylar portion having a face surface for pivotally coacting with said semispherical medial cavity of said tibial component and including a lateral condylar portion having a face surface for movably coacting with said lateral cavity of said tibial component; said face surface of said medial condylar portion having a posterior side, a distal side, an anterior side, and a semispherical shape only from a posterior point on said posterior side of said face surface of said medial condylar portion to an anterior point on said anterior side of said face surface of said medial condylar portion located about 130° from said posterior point; said face surface of said lateral condylar portion having a posterior side, a distal side, an anterior side, and a semispherical shape; said semispherical shape of said face surface of said medial condylar portion being substantially congruent with said semispherical medial cavity of said tibial component so that substantially complete surface-to-surface contact between said semispherical medial cavity of said tibial component and said face surface of said medial condylar portion of said femoral component is provided only throughout the range of flexion of about 130° of the knee joint.

2. The knee prosthesis of claim 1 in which said medial condylar portion of said femoral component includes a face surface having a posterior side, a distal side, an anterior side, and a curvature defined by a single radius of curvature in the sagittal plane from a posterior point on said posterior side of said face surface of said medial condylar portion to an anterior point on said anterior side of said face surface of said medial condylar portion.

3. The knee prosthesis of claim 1 in which said posterior point on said posterior side of said face surface of said medial condylar portion is on a transverse plane passing through the center of said single radius of curvature.

4. The knee prosthesis of claim 2 in which said anterior point on said anterior side of said face surface of said medial condylar portion is at least about 130° from said posterior point on said posterior side of said face surface of said medial condylar portion.

5. The knee prosthesis of claim 1 in which said semispherical shape of said face surface of said lateral condylar portion of said femoral component extends only from a posterior point on said posterior side of said face surface of said lateral condylar portion at least to a distal point on said distal side of said face surface of said lateral condylar portion.

6. The knee prosthesis of claim 5 in which said posterior point on said posterior side of said face surface of said lateral condylar portion is on a transverse plane passing through the center of said single radius of curvature.

7. The knee prosthesis of claim 5 in which said distal point on said distal side of said face surface of said lateral condylar portion is at least only about 90° from said posterior point on said posterior side of said face surface of said lateral condylar portion.

8. A knee prosthesis for replacing at least a portion of a knee joint between the distal end of a femur and the proximal end of a tibia; the knee prosthesis comprising:
   (a) a tibial component for mounting to the proximal end of the tibia, said tibial component including a proximal surface having a semispherical medial cavity and a lateral cavity; and
   (b) a femoral component for mounting to the distal end of the femur, said femoral component including a medial condylar portion having a face surface for pivotally coacting with said semispherical medial cavity of said tibial component and including a lateral condylar portion having a face surface for movably coacting with said lateral cavity of said tibial component; said face surface of said medial condylar portion having a spherical shape only from about 40° anterior to about 90° posterior and being substantially congruent with said semispherical medial cavity of said tibial component so that substantially complete surface-to-surface contact between said semispherical medial cavity of said tibial component and said face surface of said medial condylar portion of said femoral component is provided only throughout the range of flexion of about 130° of the knee joint.

9. A knee prosthesis for replacing at least a portion of a knee joint between the distal end of a femur and the proximal end of a tibia; the knee prosthesis comprising:
   (a) a tibial component for mounting to the proximal end of the tibia, said tibial component including a proximal surface having a semispherical medial cavity and a lateral cavity; and
   (b) a femoral component for mounting to the distal end of the femur, said femoral component including a medial condylar portion having a semispherical face surface for pivotally coacting with said semispherical medial cavity of said tibial component and including a lateral condylar portion having a face surface for movably coacting with said lateral cavity of said tibial component; said face surface of said lateral condylar portion having a spherical shape only from about 0° distal to about 90° posterior; said semi spherical face surface of said medial condylar portion being substantially congruent with said semispherical medial cavity of said tibial component so that substantially complete surface-to-surface contact between said semispherical medial cavity of said tibial component and said face surface of said medial condylar portion of said femoral component is provided throughout the range of flexion of the knee joint.

10. The knee prosthesis of claim 1 in which the center of said semispherical medial cavity of said proximal surface of said tibial component is centered about a point located generally over the posterior one third of said proximal surface of said tibial component.

11. The knee prosthesis of claim 1 in which said femoral component has a patellar flange portion joining the anterior ends of said medial and lateral condylar portions together with said medial and lateral condylar portions substantially parallel to and spaced apart from one another to form an intercondylar notch therebetween; in which said patellar flange portion has a patellar groove in the posterior or face surface thereof extending to the intercondylar notch to enable contact with a patellar component to 100° of flexion.

12. A knee prosthesis for replacing at least a portion of a knee joint between the distal end of a femur and the proximal end of a tibia; the knee prosthesis comprising:

(a) a tibial component for mounting to the proximal end of the tibia, said tibial component including a proximal surface having a semispherical medial cavity and a lateral cavity; the center of said semispherical medial cavity of said proximal surface of said tibial component being centered about a point located generally over the posterior one third of said proximal surface of said tibial component; and (b) a femoral component for mounting to the distal end of the femur, said femoral component including a medial condylar portion having a face surface for pivotally coacting with said semispherical medial cavity of said tibial component and including a lateral condylar portion having a face surface for movably coacting with said lateral cavity of said tibial component; said face surface of said medial condylar portion of said femoral component having a posterior side, a distal side, an anterior side, and a semispherical shape that extends only from a posterior point on said posterior side of said face surface of said medial condylar portion to an anterior point on said anterior side of said face surface of said medial condylar portion located about 130° from said anterior point; said semispherical shape of said face surface of said medial condylar portion being substantially congruent with said semispherical medial cavity of said tibial component so that substantially complete surface-to-surface contact between said semispherical medial cavity of said tibial component and said semispherical medial condylar portion of said femoral component is provided only throughout the range of flexion of about 130° of the knee joint; said face surface of said lateral condylar portion of said femoral component having a posterior side, a distal side, an anterior side, and a semispherical shape that extends only from a posterior point on said posterior side of said face surface of said lateral condylar portion to a distal point on said distal side of said face surface of said lateral condylar portion located about 90° from said posterior point.

* * * * *